US006495742B1

(12) United States Patent
Shinozaki et al.

(10) Patent No.: US 6,495,742 B1
(45) Date of Patent: Dec. 17, 2002

(54) GENES ENCODING PLANT TRANSCRIPTION FACTORS

(75) Inventors: Kazuko Shinozaki, Ibaraki (JP); Mie Kasuga, Ibaraki (JP)

(73) Assignees: Independent Administrative Institute Japan International Research Center for Agricultural Sciences, Tusukuba (JP); Bio-oriented Technology Research Advancement Institution, Omiya (JP)

( * ) Notice: Subject to any disclaimer, the term of this patent is extended or adjusted under 35 U.S.C. 154(b) by 0 days.

(21) Appl. No.: 09/301,666

(22) Filed: Apr. 28, 1999

(30) Foreign Application Priority Data

Aug. 12, 1998 (JP) ............................................. 10-228457

(51) Int. Cl.[7] ........................ C07H 21/04; C12N 15/74; C12N 15/82; C12N 15/29; A01H 5/00
(52) U.S. Cl. .................... 800/298; 435/320.1; 435/419; 435/252.3; 536/23.6; 800/289
(58) Field of Search ............................. 435/320.1, 419, 435/252.3; 536/23.6; 800/295, 298, 289

(56) References Cited

U.S. PATENT DOCUMENTS 5,891,859 A * 4/1999 Thomashow et al.

OTHER PUBLICATIONS

Liu et al, Two Transcription Factors, DREB1 and DREB2, with an EREBP/AP2 DNA Binding Domain Seperate Two Cell. Signal Transduction Pathways in Drought–and Low–Temp.Respon.Gene Express Respect. in Arabidopsis, Aug. 1998, The Plant Cell, vol. 10, pp 1391–1406.*

Jaglo–Ottosen et al, Arabidopsis CBF1 Overexpression Induces COR Genes and Enhances Freezing Tolerance, Apr. 1998, Science, vol. 280, pp. 104–106.*
Abstract: Lui, Qiang et al., Analysis of DREB Gene Encoding a Protein Binding to the cis–Element DRE which Stimulates Dehydration/Low Temperature Stress–Responsive Gene Expression in *Arabidopsis Thaliana*. 1998 Annual Meeting and the 38th Symposium of the Japanese Society of Plant Physiologists, May 3–5, 1998, F3a–11.
Abstract: Miura, Setsuko, et al., Analysis of *Arabidopsis thaliana*, in which the Dehydration/Salt/Low Temperature Stress Inducible Transcription Factor DREB1A or DREB2A is Over–expressed. 1998 Annual Meeting and the 38th Symposium of the Japanese Society of Plant Physiologists, May 3–5, 1998, F3a–12.
Abstract: Shirjwari, Zabta K., et al., Identification of the DREB1B Family Encoding Proteins which Bind to the Dehydration/Low Temperature Responsive Element DRE of *Arabidopsis thaliana* and Analysis of Expression of the Family. 1998 Annual Meeting and the 38th Symposium of the Japanese Society of Plant Physiologists, May 3–5, 1998, F3a–13.

* cited by examiner

*Primary Examiner*—David T. Fox
*Assistant Examiner*—David H Kruse
(74) *Attorney, Agent, or Firm*—Davidson, Davidson & Kappel, LLP

(57) ABSTRACT

According to the present invention, a protein which binds to DRE to activate the transcription of genes located downstream of the DRE, a gene encoding the protein, a recombinant vector comprising the gene, a transformant comprising the recombinant vector, a transgenic plant comprising the gene, and a method for producing the gene using the transformant are provided. The present invention is useful for creating a stress tolerant plant.

6 Claims, 6 Drawing Sheets

A

Effector Plasmid

Reporter Plasmid

B

35S:DREB1A

GENES ENCODING PLANT TRANSCRIPTION FACTORS

This application is related to the co-pending application, ENVIRONMENTAL STRESS-TOLERANT PLANTS, U.S. application Ser. No. 09/301,217, filed on Apr. 28, 1999.

BACKGROUND OF THE INVENTION

1. Field of the Invention

The present invention relates to a protein which binds to a stress responsive element and regulates the transcription of genes located downstream of the element; a gene coding for the above protein; a recombinant vector comprising the gene; a transformant comprising the recombinant vector; a transgenic plant comprising the gene; a method for producing the above protein using the transformant; and a method for determining a stress level in a plant.

2. Prior Art

Transcription of genes is performed by RNA polymerase. RNA polymerase synthesizes ribonucleoside phosphates in the 5' to 3' direction using double-stranded DNA as a template in a primer independent manner. In the case of *Escherichia coli*, for example, its RNA polymerase takes the form of a holoenzyme in which ρ factor having promoter recognition ability is bound to the core enzyme $β'βα_2$. This RNA polymerase initiates transcription and elongates RNA chain; the transcription is terminated by the binding of ρ factor. On the other hand, in the case of eucaryotes, RNA polymerase is classified into RNA polymerases I, II and III, any of which has a complicated structure composed of more than 10 subunits. RNA polymerase I selectively transcribes rRNA; RNA polymerase II selectively transcribes mRNA precursor; and RNA polymerase III selectively transcribes tRNA and 5SrRNA. The amount of RNA synthesized by such RNA polymerase varies widely depending on the growth stage of the relevant cells and environmental changes around them. A transcription factor which positively or negatively regulates the transcription initiation of RNA polymerase is deeply involved in the variation in the amount of RNA synthesis.

Generally, living cells are exposed to an external environment composed of a number of factors including temperature, pressure, oxygen, light, radioactive rays, metal ions, organic compounds, etc. When these factors vary, cells perceive such changes as stress and make characteristic responses to them. For example, cells exhibit a response called "heat shock response" to high temperatures. From this response, the expression of a group of heat shock proteins (HSPs) is induced. HSPs prevent the irreversible precipitation of heat-denatured proteins and have the function of molecular chaperone that facilitates the refolding of such proteins, thereby protecting cells from heat stress. It is known that a transcription factor called "heat shock factor (HSF)" plays an important role in the manifestation of the above-described heat shock response in human, Xenopus, Drosophila, etc. [Kazuhiro Nagata, Cell Technology, 10:348–356 (1991)]. When activated by heat shock, HSF binds to heat shock element (HSE) located upstream of a gene coding for HSP (also known as heat shock gene) to thereby promote the transcription of the heat shock gene.

On the other hand, it is also reported that plants induce stress proteins such as LEA proteins, water channel proteins or synthetases for compatible solutes in their cells when they are exposed to stress such as dehydration, low temperature, freezing or salt, thereby protecting their cells from such stress. However, much more research is required to elucidate transcription factors which regulate the transcription of genes encoding those stress proteins.

OBJECTS AND SUMMARY OF THE INVENTION

It is an object of the present invention to provide a protein which regulates the transcription of genes located downstream of a stress responsive element which is essential for controlling stress responsive gene expression; a gene encoding the protein; a recombinant vector comprising the gene; a transformant comprising the recombinant vector; a transgenic plant comprising the gene; a method for producing the above protein using the transformant; and a method for determining a stress level in a plant.

As a result of extensive and intensive researches toward the solution of the above-described problem, the present inventors have succeeded in isolating from a low temperature resistant plant *Arabidopsis thaliana* a gene coding for a transcription factor which binds to a stress responsive element and activates the transcription of genes located downstream of the element. Thus, the present invention has been achieved.

The present invention relates to the following recombinant protein (a) or (b):

(a) a protein consisting of the amino acid sequence as shown in SEQ ID NO: 2, SEQ ID NO: 4, SEQ ID NO: 8 or SEQ ID NO: 10;

(b) a protein which consists of the amino acid sequence having deletion, substitution or addition of at least one amino acid in the amino acid sequence as shown in SEQ ID NO: 2, SEQ ID NO: 4, SEQ ID NO: 8 or SEQ ID NO: 10 and which regulates the transcription of genes located downstream of a stress responsive element.

Further, the present invention relates to a transcription factor gene coding for the following protein (a) or (b):

(a) a protein consisting of the amino acid sequence as shown in SEQ ID NO: 2, SEQ ID NO: 4, SEQ ID NO: 8 or SEQ ID NO: 10;

(b) a protein which consists of the amino acid sequence having deletion, substitution or addition of at least one amino acid in the amino acid sequence as shown in SEQ ID NO: 2, SEQ ID NO: 4, SEQ ID NO: 8 or SEQ ID NO: 10 and which regulates the transcription of genes located downstream of a stress responsive element.

Further, the present invention relates to a gene comprising the following DNA (c) or (d):

(c) a DNA consisting of the nucleotide sequence as shown in SEQ ID NO: 1, SEQ ID NO: 3, SEQ ID NO: 7 or SEQ ID NO: 9;

(d) a DNA which hybridizes with the DNA consisting of the nucleotide sequence as shown in SEQ ID NO: 1, SEQ ID NO: 3, SEQ ID NO: 7 or SEQ ID NO: 9 under stringent conditions and which codes for a protein that regulates the transcription of genes located downstream of a stress responsive element.

Specific examples of the above-mentioned stress include dehydration stress, low temperature stress and salt stress.

Further, the present invention relates to a recombinant vector comprising the gene of the invention.

Further, the present invention relates to a transformant comprising the recombinant vector.

Further, the present invention relates to a transgenic plant comprising the gene of the invention.

Further, the present invention relates to a method for producing a protein which regulates the transcription of genes located downstream of a stress responsive element, comprising culturing the above transformant in a medium and recovering the protein from the resultant culture.

Further, the present invention relates to a method for determining a stress level in a plant, comprising determining a transcription level of the gene of the invention in the plant.

DETAILED DESCRIPTION OF THE INVENTION

Figure 1:
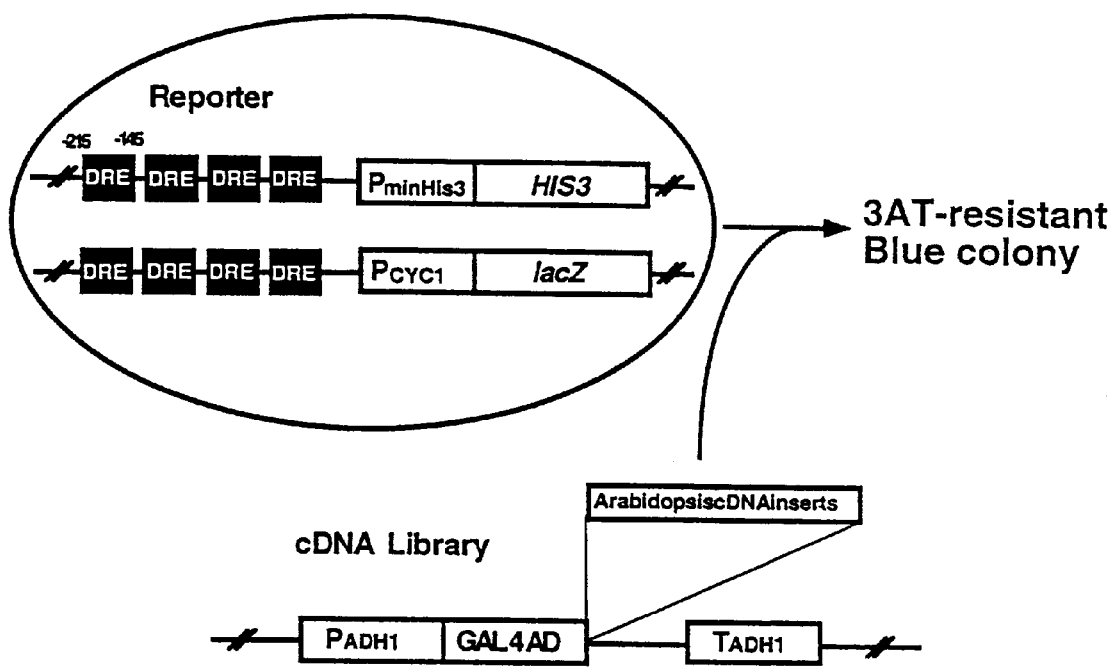
FIG. 1 is a diagram showing the principle of screening of the gene of the invention.

Hereinbelow, the present invention will be described in detail.

The gene of the invention is a gene encoding a protein (transcription factor) which binds to a cis element located upstream of genes encoding stress responsive proteins expressed in response to environmental stresses such as low temperature, dehydration or salt, to thereby activate the transcription of the genes of those stress responsive proteins. Specific examples of the above cis element include dehydration responsive element (DRE), abscisic acid responsive element (ABRE) and low temperature responsive element. The protein encoded by the gene of the invention has a function to activate the transcription of genes located downstream of the above-mentioned stress responsive element.

In the present invention, genes encoding DRE-binding proteins will be explained by way of example. Hereinafter, the genes of the invention are referred to as "DRE-binding protein 1A gene" (also called "DREB1A gene"), "DRE-binding protein 1C gene" (also called "DREB1C gene"), "DRE-binding protein 2A gene" (also called "DREB2A gene") and "DRE-binding protein 2B gene" (also called "DREB2B gene").

1. Cloning of the Gene of the Invention
1-1. Preparation of mRNA and a cDNA Library from *Arabidopsis thaliana*.

As a source of mRNA, a part of the plant body of *Arabidopsis thaliana* such as leaves, stems, roots or flowers, or the plant body as a whole may be used. Alternatively, plant bodies obtained by sowing seeds of *Arabidopsis thaliana* on a solid medium such as GM medium, MS medium or #3 medium and growing them aseptically may be used. The mRNA level of DREB1A gene of the invention in *Arabidopsis thaliana* plants increases when they are exposed to low temperature stress (e.g. 10 to −4° C.). On the other hand, the mRNA level of DREB2A gene of the invention increases when the plants are exposed to salt stress (e.g. 150–250 mM NaCl) or dehydration stress (e.g. dehydrated state). Therefore, *Arabidopsis thaliana* plants which have been exposed to such stress may also be used.

mRNA is prepared, for example, by exposing *Arabidopsis thaliana* plant bodies grown on GM medium to low temperature stress, dehydration stress or salt stress and then freeze them with liquid nitrogen. Subsequently, conventional techniques for mRNA preparation may be used. For example, the frozen plant bodies are ground in a mortar. From the resultant ground material, crude RNA fraction is extracted by the glyoxal method, the guanidine thiocyanate-cesium chloride method, the lithium chloride-urea method, the proteinase K-deoxyribonuclease method or the like. From this crude RNA fraction, poly(A)$^+$ RNA (mRNA) can be obtained by the affinity column method using oligo dT-cellulose or poly U-Sepharose carried on Sepharose 2B or by the batch method. The resultant mRNA may further be fractionated by sucrose gradient centrifugation or the like.

Single-stranded cDNA is synthesized using the thus obtained mRNA as a template; this synthesis is performed using a commercial kit (e.g. ZAP-cDNA Synthesis Kit: Stratagene), oligo(dT)$_{20}$ and a reverse transcriptase. Then, double-stranded cDNA is synthesized from the resultant single-stranded cDNA. An appropriate adaptor such as EcoRI-NotI-BamHI adaptor is added to the resultant double-stranded cDNA, which is then ligated downstream of a transcriptional activation domain (such as GAL4 activation domain) in a plasmid (such as pAD-GAL4 plasmid: Stratagene) containing such a domain to thereby prepare a cDNA library.

1-2. A Host to be Used in the Cloning of the Gene of the Invention

The gene of the invention can be cloned, for example, by one hybrid screening using yeast. The screening by this method may be performed using a commercial kit (e.g. Matchmaker One Hybrid System: Clontech).

In the cloning of the gene of the invention using the above-mentioned kit, first, a DNA comprising DRE sequences to which the transcription factor of the invention binds is ligated to both plasmids pHISi-1 and pLacZi contained in the kit. The thus constructed plasmids are transformed into the yeast contained in the kit (*Saccharomayces cerevisiae* YM4271) to thereby prepare a host yeast for cloning.

The host yeast for cloning can biosynthesize histidine by the action of HIS3 protein which is expressed leakily by HIS3 minimum promoter. Thus, this yeast can survive in the absence of histidine. However, since the promoter used for the expression of the gene encoding HIS3 protein is a minimum promoter which can only maintain the minimum transcription level, HIS3 protein produced in cells is extremely small in quantity. Therefore, when the host yeast is cultured in the presence of 3-AT (3-aminotriazole) that is a competitive inhibitor against HIS protein, the function of HIS3 protein in cells is inhibited by 3-AT in a concentration dependent manner. When the concentration of 3-AT exceeds a specific level, HIS3 protein in cells becomes unable to function and, as a result, the host yeast becomes unable to grow in the absence of histidine.

Since lacZ gene is also located downstream of CYC1 minimum promoter, β-galactosidase is produced only in extremely small quantity in the yeast cells. Thus, when the host yeast is plated on an Xgal containing plate, colonies appearing thereon do not have such Xgal degrading ability that turns the colonies into blue as a whole. However, when a transcription factor that binds to DRE located upstream of HIS3 and lacZ genes to activate the transcription thereof is expressed in the host yeast, the yeast becomes viable in the presence of 3-AT and, at the same time, Xgal is degraded to turn the colonies into blue.

As used herein, the term "dehydration responsive element (DRE)" refers to a cis-acting DNA domain consisting of a 9 bp conserved sequence 5'-TACCGACAT-3' located upstream of those genes which are expressed upon exposure to dehydration stress, low temperature stress, etc.

A DNA region comprising DRE can be obtained by amplifying the promoter region (from −215 to −145 based on the translation initiation site) of rd29A gene [Kazuko Yamaguchi-Shinozaki and Kazuo Shinozaki, The Plant Cell 6:251–264 (1994)], one of dehydration tolerance genes, by polymerase chain reaction (PCR). As a template DNA which can be used in this PCR, genomic DNA from *Arabidopsis thaliana* is given. As a sense primer, 5'-aagcttaagcttacatcagt ttgaaagaaa-3' (SEQ ID NO: 11) may be used. As an antisense primer, 5'-aagcttaagcttgcttttggaactcatgtc- 3' (SEQ ID NO: 12) may be used. Other primers may also be used in the present invention.

1-3. Cloning of DREB2A Gene and DREB2A Gene

DREB2A gene and DREB2A gene of the invention can be obtained by transforming the cDNA library obtained in subsection 1-1 above into the host obtained in subsection 1-2 above by the lithium acetate method or the like, plating the resultant transformant on LB medium plate or the like containing Xgal (5-bromo-4-chloro-3-indolyl- β-D-galactoside) and 3-AT (3-aminotriazole), culturing the transformant, selecting blue colonies appearing on the plate and isolating the plasmids therefrom.

Briefly, a positive clone containing DREB1A gene or DREB2A gene of the invention contains a fusion gene composed of a DNA region coding for GAL4 activation domain (GAL4 AD) and a DNA region coding for DRE-binding protein, and expresses a fusion protein (hybrid protein) composed of DRE-binding protein and GAL4 activation domain. Subsequently, the expressed fusion protein binds, through DRE-binding protein, to DRE located upstream of a reporter gene. Then, GAL4 activation domain activates the transcription of lacZ gene and HIS3 gene. As a result, the positive clone produces remarkable amounts of HIS3 protein and β-galactosidase. Thus, because of the action of the HIS3 protein abundantly produced, the positive clone can biosynthesize histidine even in the presence of 3-AT. Therefore, the clone becomes viable in the presence of 3-AT and, at the same time, the Xgal in the medium is degraded by the β-galactosidase produced to turn the colonies into blue.

Subsequently, these colonies are subjected to single cell isolation. The isolated cells are cultured. Then, plasmid DNA is purified from the cultured cells to thereby obtain DREB1A gene or DREB2A gene of the invention.

1-4. Homologues to DREB1A Protein or DREB2A Protein

Organisms may have a plurality of genes with similar nucleotide sequences which are considered to have evolved from a single gene. Proteins encoded by such genes are mutually called homologues. They can be cloned from the relevant gene library using as a probe a part of the gene of which the nucleotide sequence has already been known. In the present invention, genes encoding homologues to DREB1A or DREB2A protein can be cloned from the *Arabidopsis thaliana* cDNA library using DREB1A cDNA or DREB2A cDNA obtained in subsection 1-3 above as a probe.

1-5. Determination of Nucleotide Sequences

The cDNA portion is cut out from the plasmid obtained in subsection 1-3 or 1-4 above using a restriction enzyme and ligated to an appropriate plasmid such as pSK (Stratagene) for sub-cloning. Then, the entire nucleotide sequence is determined. Sequencing can be performed by conventional methods such as the chemical modification method by Maxam-Gilbert or the dideoxynucleotide chain termination method using M13 phage. Usually, sequencing is carried out with an automated DNA sequencer (e.g. Perkin-Elmer Model 373A DNA Sequencer).

SEQ ID NOS: 1, 3, 7 and 9 show nucleotide sequences for the genes of the invention, and SEQ ID NOS: 2, 4, 8 and 10 show amino acid sequences for the proteins of the invention. As long as a protein consisting of one of these amino acid sequences has a function to bind to DRE to thereby activate the transcription of genes located downstream of DRE, the amino acid sequence may have mutation (such as deletion, substitution or addition) in at least one amino acid.

For example, at least 1 amino acid, preferably 1 to about 20 amino acids, more preferably 1 to 5 amino acids may be deleted in the amino acid sequence shown in SEQ ID NO: 2, 4, 8 or 10; at least 1 amino acid, preferably 1 to about 20 amino acids, more preferably 1 to 5 amino acids may be added to the amino acid sequence shown in SEQ ID NO: 2, 4, 8 or 10; or at least 1 amino acid, preferably 1 to about 160 amino acids, more preferably 1 to 40 amino acids may be substituted with other amino acid(s) in the amino acid sequence shown in SEQ ID NO: 2, 4, 8 or 10.

Also, a DNA which can hybridize with the above-mentioned gene under stringent conditions is included in the gene of the invention. The "stringent conditions" means, for example, those conditions in which formamide concentration is 30–50%, preferably 50%, and temperature is 37–50° C., preferably 42° C.

The introduction of mutation into the gene of the invention may be performed by known techniques such as the method of Kunkel, the gapped duplex method or variations thereof using a mutation introducing kit [e.g. Mutant-K (Takara) or Mutant-G (Takara)] utilizing site-directed mutagenesis or using a LA PCR in vitro Mutagenesis Series Kit (Takara).

Once the nucleotide sequence for the gene of the invention has been determined definitely, the gene of the invention can be obtained by chemical synthesis, by PCR using the cDNA or genomic DNA of the gene of the invention as a template, or by hybridization of a DNA fragment having the above nucleotide sequence as a probe.

The recombinant vectors of the invention were introduced into *E coli* K-12 strain and deposited at the National Institute of Bioscience and Human-Technology, Agency of Industrial Science and Technology (1-3, Higashi 1-Chome, Tsukuba City, Ibaraki Pref., Japan) as FERM BP-6654 (DREB1A gene-introduced strain) and FERM BP-6655 (DREB2A gene-introduced strain) on Aug. 11, 1998.

2. Determination of the DRE Binding Ability and Transcription Activating Ability of the Proteins of the Invention 2-1. Analysis of the DRE Binding Ability of DREB1A and DREB2A Proteins The ability of DREB1A or DREB2A protein to bind to DRE can be confirmed by performing a gel shift assay [Urao, T. et al., Plant Cell 5:1529–1539 (1993)] using a fusion protein composed of DREB1A or DREB2A protein and GST. The fusion protein composed of DREB1A or DREB2A protein and GST can be prepared by ligating DREB1A or DREB2A gene downstream of the GST (glutathione-S-transferase) coding region of a plasmid containing GST gene (e.g. pGEX-4T-1 vector: Pharmacia) so that the reading frames of the two genes coincide with each other, transforming the resultant plasmid into *E. coli*, culturing the *E. coli* under conditions which induce synthesis of the fusion protein and purifying the fusion protein from the resultant culture.

Gel shift assay is a method for examining the interaction between a DNA and a protein. Briefly, DRE-containing DNA fragment labelled with $^{32}$P or the like is mixed with the fusion protein described above and incubated. The resultant mixture is electrophoresed. After drying, the gel is autoradiographed to detect those bands which have migrated behind as a result of the binding of the DNA fragment and the protein. In the present invention, the specific binding of DREB1A or DREB2A protein to the DRE sequence can be confirmed by making it clear that the above-mentioned behind band is not detected when a DNA fragment containing a varied DRE sequence is used.

2-2. Analysis of the Transcription Activating Ability of the Proteins of the Invention The transcription activating ability of the proteins of the invention can be analyzed by a trans activation experiment using a protoplast system from *Arabidopsis thaliana*. For example, DREB1A cDNA is ligated to pBI221 plasmid (Clontech) containing CaMV35S promoter to construct an effector plasmid. On the other hand, 3 cassettes of the DRE-containing 71 base DNA region obtained in subsection 1-2 above are connected tandemly to prepare a DNA fragment, which is ligated upstream of TATA promoter located upstream of β-glucuronidase (GUS) gene in pBI221 plasmid to construct a reporter plasmid. Subsequently, these two plasmids are introduced into protoplasts of *Arabidopsis thaliana* and then GUS activity is determined. If GUS activity is increased by the simultaneous expression of DREB1A protein, it is understood that DREB1A protein expressed in the protoplasts is activating the transcription of GUS gene through the DRE sequence.

In the present invention, preparation of protoplasts and introduction of plasmid DNA into the protoplasts may be performed by the method of Abel et al. [Abel, S. et al., Plant J. 5:421–427 (1994)]. In order to minimize experimental errors resulted from the difference in plasmid DNA introduction efficiency by experiment, a plasmid in which luciferase gene is ligated downstream of CaMV35S promoter may be introduced to protoplasts together with the two plasmids described above, and β-glucuronidase activity against luciferase activity may be determined. Then, the determined value may be taken as a value indicating the transcription activating ability. β-glucuronidase activity can be determined by the method of Jefferson [Jefferson, R. A., EMBO J. 83:8447–8451 (1986)]; and luciferase activity can be determined using PicaGene Luciferase Assay Kit (Toyo Ink).

3. Preparation of Recombinant Vectors and Transformants 3-1. Preparation of Recombinant Vectors The recombinant vector of the invention can be obtained by ligating (inserting) the gene of the invention to (into) an appropriate vector. The vector into which the gene of the invention is to be inserted is not particularly limited as long as it is replicable in a host. For example, plasmid DNA, phage DNA or the like may be used.

Specific examples of plasmid DNA include plasmids for *E coli* hosts such as pBR322, pBR325, pUC118, pUC119; plasmids for *Bacillus subtilis* hosts such as pUB110, pTP5; plasmids for host yeasts such as YEp13, YEp24, YCp50; and plasmids for host plant cells such as pBI221, pBI121. Specific examples of phage DNA include λ phage and the like. Further, an animal virus vector such as retrovirus or vaccinia virus; or an insect virus vector such as baculovirus may also be used.

For insertion of the gene of the invention into a vector, a method may be employed in which the purified DNA is digested with an appropriate restriction enzyme and then inserted into the restriction site or the multi-cloning site of an appropriate vector DNA for ligation to the vector.

The gene of the invention should be operably incorporated into the vector. For this purpose, the vector of the invention may contain, if desired, cis elements (such as enhancer), a splicing signal, poly(A) addition signal, selection marker, ribosome binding sequence (SD sequence) or the like in addition to a promoter and the gene of the invention. As the selection marker, dihydrofolate reductase gene, ampicillin resistance gene, neomycin resistance gene, or the like may be enumerated.

3-2. Preparation of Transformants

The transformant of the invention can be obtained by introducing the recombinant vector of the invention into a host so that the gene of interest can be expressed. The host is not particularly limited as long as it can express the gene of the invention. Specific examples of the host include Escherichia bacteria such as *E coli*; Bacillus bacteria such as *Bacillus subtilis*; Pseudomonas bacteria such as *Pseudomonas putida*; Rhizobium bacteria such as *Rhizobium meliloti*; yeasts such as *Saccharomyces cerevisiae, Schizosaccharomyces pombe*; plant cell strains established from *Arabidopsis thaliana*, tobacco, maize, rice, carrot, etc. or protoplasts prepared from such plants; animal cells such as COS cells, CHO cells; or insect cells such as Sf9 cells, Sf21 cells.

When a bacterium such as *E coli* is used as the host, the recombinant vector of the invention is capable of autonomous replication in the host and, at the same time, it is preferably composed of a promoter, a ribosome binding sequence, the gene of the invention and a transcription termination sequence. The vector may also contain a gene to control the promoter.

As *E coli*, HMS174 (DE3), K12 or DH1 strain may be used, for example. As *Bacillus subtilis*, MI 114 or 207-21 strain may be used, for example.

As the promoter, any promoter may be used as long as it can direct the expression of the gene of interest in a host such as *E. coli*. For example, an *E coli*- or phage-derived promoter such as trp promoter, lac promoter, $P_L$ promoter or $P_R$ promoter may be used. An artificially designed and altered promoter such as tac promoter may also be used.

As a method for introducing the recombinant vector into a bacterium, any method of DNA introduction into bacteria may be used. For example, a method using calcium ions [Cohen, S. N. et al., Proc. Natl. Acad. Sci., USA, 69:2110–2114 (1972)], electroporation, or the like may be used.

When a yeast is used as the host, *Saccharomyces cerevisiae, Schizosaccharomyces pombe, Pichia pastoris* or the like is used. In this case, the promoter to be used is not particularly limited. Any promoter may be used as long as it can direct the expression of the gene of interest in yeast. For example, gal1 promoter, gal10 promoter, heat shock protein promoter, MFα1 promoter, PH05 promoter, PGK promoter, GAP promoter, ADH promoter, AOX1 promoter or the like may be enumerated.

As a method for introducing the recombinant vector into yeast, any method of DNA introduction into yeast may be used. For example, electroporation [Becker, D. M. et al., Methods Enzymol., 194:182–187 (1990)], the spheroplast method [Hinnen, A. et al., Proc. Natl. Acad. Sci., USA, 75:1929–1933 (1978)], the lithium acetate method [Itoh, H., J. Bacteriol., 153:163–168 (1983)] or the like may be enumerated.

When a plant cell is used as the host, a cell strain established from *Arabidopsis thaliana*, tobacco, maize, rice, carrot, etc. or a protoplast prepared from such plants may be used. In this case, the promoter to be used is not particularly limited as long as it can direct the expression of the gene of interest in plants. For example, 35S RNA promoter of cauliflower mosaic virus, rd29A gene promoter, rbcS promoter or the like may be enumerated.

As a method for introducing the recombinant vector into a plant, the method of Abel et al. using polyethylene glycol [Abel, H. et al., Plant J. 5:421–427 (1994)], electroporation or the like may be used.

When an animal cell is used as the host, simian COS-7 or Vero cells, Chinese hamster ovary cells (CHO cells), mouse L cells, rat GH3 cells, human FL cells or the like may be used. As a promoter, SRα promoter, SV40 promoter, LTR promoter, CMV promoter or the like may be used. The early gene promoter of human cytomegalovirus may also be used.

As a method for introducing the recombinant vector into an animal cell, electroporation, the calcium phosphate method, lipofection or the like may be enumerated.

When an insect cell is used as the host, Sf9 cells, Sf21 cells or the like may be used.

As a method for introducing the recombinant vector into an insect cell, the calcium phosphate method, lipofection, electroporation or the like may be used.

4. Production of the Proteins of the Invention

The protein of the invention is a protein having the amino acid sequence encoded by the gene of the invention; or a protein which has the above amino acid sequence having the mutation described above at least at one amino acid and yet which has a function to regulate the transcription of genes located downstream of a stress responsive element. In this specification, the protein encoded by DREB1A gene is called "DREB1A protein"; the protein encoded by DREB1B gene is called "DREB1B protein"; the protein encoded by DREB1C gene is called "DREB1C protein"; the protein encoded by DREB2A gene is called "DREB2A protein"; and the protein encoded by DREB2B gene is called "DREB2B protein".

The protein of the invention can be obtained by culturing the transformant described above in a medium and recovering the protein from the resultant culture. The term "culture" means any of the following materials: culture supernatant, cultured cells, cultured microorganisms, or disrupted cells or microorganisms.

The cultivation of the transformant of the invention in a medium is carried out by conventional methods used for culturing a host.

As a medium for culturing the transformant obtained from a microorganism host such as *E. coli* or yeast, either a natural or synthetic medium may be used as long as it contains carbon sources, nitrogen sources and inorganic salts assimilable by the microorganism and is capable of efficient cultivation of the transformant. When a plant cell is used as the host, vitamins such as thiamine and pyridoxine are added to the medium if necessary. When an animal cell is used as the host, a serum such as RPMI1640 is added to the medium if necessary.

As carbon sources, carbohydrates such as glucose, fructose, sucrose, starch; organic acids such as acetic acid, propionic acid; and alcohols such as ethanol and propanol may be used.

As nitrogen sources, ammonia; ammonium salts of inorganic or organic acids such as ammonium chloride, ammonium sulfate, ammonium acetate, ammonium phosphate; other nitrogen-containing compounds; Peptone; meat extract; corn steep liquor and the like may be used.

As inorganic substances, potassium dihydrogen phosphate, dipotassium hydrogen phosphate, magnesium phosphate, magnesium sulfate, sodium chloride, iron(II) sulfate, manganese sulfate, copper sulfate, calcium carbonate and the like may be used.

Usually, the cultivation is carried out under aerobic conditions (such as shaking culture or aeration agitation culture) at 37° C. for 6 to 24 hrs. During the cultivation, the pH is maintained at 7.0 to 7.5. The pH adjustment is carried out with an inorganic or organic acid, an alkali solution or the like.

During the cultivation, an antibiotic such as ampicillin or tetracycline may be added to the medium if necessary.

When a microorganism transformed with an expression vector containing an inducible promoter is cultured, an inducer may be added to the medium if necessary. For example, when a microorganism transformed with an expression vector containing Lac promoter is cultured, isopropyl-β-D-thiogalactopyranoside (IPTG) or the like may be added. When a microorganism transformed with an expression vector containing trp promoter is cultured, indoleacrylic acid (IAA) or the like may be added.

Usually, the cultivation of such a microorganism is carried out in the presence 5% $CO_2$ at 37° C. for 1 to 30 days. During the cultivation, an antibiotic such as kanamycin or penicillin may be added to the medium if necessary.

After the cultivation, the protein of the invention is extracted by disrupting the cultured microorganisms or cells if the protein is produced in the microorganisms or cells. If the protein of the invention is produced outside of the microorganisms or cells, the culture fluid is used as it is or subjected to centrifugation to remove the microorganisms or cells. Thereafter, the resultant supernatant is subjected to conventional biochemical techniques used for isolating/ purifying a protein. These techniques include ammonium sulfate precipitation, gel chromatography, ion exchange chromatography and affinity chromatography; these techniques may be used independently or in an appropriate combination to thereby isolate and purify the protein of the invention from the above culture.

5. Creation of Transgenic Plants into which the Gene of the Invention is Introduced A transgenic plant resistant to environmental stresses, in particular, low temperature stress, freezing stress and dehydration stress, can be created by introducing a DNA encoding the protein of the invention into a host plant using recombinant techniques. As a method for introducing the gene of the invention into a host plant, indirect introduction such as the Agrobacterium infection method, or direct introduction such as the particle gun method, polyethylene glycol method, liposome method, microinjection method or the like may be used. When the Agrobacterium infection method is used, the transgenic plant of the invention can be created by the following procedures.

5-1. Preparation of a Recombinant Vector to be Introduced into a Plant and Transformation of Agrobacterium A recombinant vector to be introduced into a plant can be prepared by digesting with an appropriate restriction enzyme a DNA comprising DREB1A, DREB1C, DREB2A or DREB2B gene obtained in section 1 above, ligating an appropriate linker to the resultant DNA if necessary, and inserting the DNA into a cloning vector for plant cells. As the cloning vector, a binary vector type plasmid such as pBI2113Not, pBI2113, pBI101, pBI121, pGA482, pGAH, pBIG; or an intermediate vector type plasmid such as pLGV23Neo, pNCAT, pMON200 may be used.

When a binary vector type plasmid is used, the gene of interest is inserted between the border sequences (LB, RB) of the binary vector. The resultant recombinant vector is amplified in E. coli. The amplified recombinant vector is introduced into Agrobacterium tumefaciens C58, LBA4404, EHA101, C58C1Rif$^R$, EHA105, etc. by freeze-thawing, electroporation or the like. The resultant Agrobacterium tumefaciens is used for the transformation of a plant of interest.

In addition to the method described above, the three-member conjugation method [Nucleic Acids Research, 12:8711 (1984)] may also be used to prepare an Agrobacterium containing the gene of the invention for use in plant infection. Briefly, an E. coli containing a plasmid comprising the gene of interest, an E. coli containing a helper plasmid (e.g. pRK2013) and an Agrobacterium are mixed and cultured on a medium containing rifampicin and kanamycin. Thus, a zygote Agrobacterium for infecting plants can be obtained.

For the expression of a foreign gene in a plant body, a promoter and a terminator for plants should be located before and after the structural gene of the foreign gene, respectively. Specific examples of promoters which may be utilized in the present invention include cauliflower mosaic virus (CaMV)-derived 35S transcript [Jefferson, R. A. et al., The EMBO J. 6:3901–3907 (1987)]; the promoter for maize ubiquitin gene [Christensen, A. H. et al., Plant Mol. Biol. 18:675–689 (1992)]; the promoter for nopaline synthase (NOS) gene and the promoter for octopin (OCT) synthase gene. Specific examples of useful terminator sequences include CaMV-derived terminator and NOS-derived terminator. Other promoters and terminators which are known to function in plant bodies may also be used in the present invention.

If the promoter used in a transgenic plant is a promoter responsible for the constitutive expression of the gene of interest (e.g. CaMV 35S promoter) and the use thereof has brought about delay in the growth of the transgenic plant or dwarfing of the plant, a promoter which directs transient expression of the gene of interest (e.g. rd29A gene promoter) may be used.

If necessary, an intron sequence which enhances the expression of the gene of the invention may be located between the promoter sequence and the gene. For example, the intron from maize alcohol dehydrogenase (Adh1) [Genes & Development 1:1183–1200 (1987)] may be introduced.

In order to select transformed cells of interest efficiently, it is preferable to use an effective selection marker gene in combination with the gene of interest. As the selection marker, one or more genes selected from kanamycin resistance gene (NPTII), hygromycin phosphotransferase gene (htp) which confers resistance to the antibiotic hygromycin on plants, phosphinothricin acetyl transferase gene (bar) which confers resistance to bialaphos and the like.

The gene of the invention and the selection marker gene may be incorporated together into a single vector. Alternatively, the two genes may be incorporated into separate vectors to prepare two recombinant DNAs.

5-2. Introduction of the Gene of the Invention into a Host Plant

In the present invention, the term "host plant" means any of the following: cultured plant cells, the entire plant body of a cultured plant, plant organs (such as leaves, petals, stems, roots, rhizomes, seeds), or plant tissues (such as epidermis, phloem, parenchyma, xylem, vascular bundle). Specific examples of plants which may be used as a host include Arabidopsis thaliana, tobacco, rice and maize.

When a cultured plant cell, plant body, plant organ or plant tissue is used as a host plant, a DNA encoding the protein of the invention is incorporated into a vector, which is then introduced into plant sections by the Agrobacterium infection method, particle gun method or polyethylene glycol method to thereby transform the host plant. Alternatively, the DNA may be directly introduced to protoplasts by electroporation to thereby create a transformed plant.

If the gene of interest is introduced by the Agrobacterium infection method, a step of infecting the plant with an Agrobacterium containing a plasmid comprising the gene of interest is essential. This step can be performed by the vacuum infiltration method [CR Acad. Sci. Paris, Life Science, 316:1194 (1993)]. Briefly, Arabidopsis thaliana is grown in a soil composed of vermiculite and perlite (50:50). The resultant plant is dipped directly in a culture fluid of an Agrobacterium containing a plasmid comprising the gene of the invention, placed in a desiccator and then sucked with a vacuum pump to 65–70 mmHg. Then, the plant was allowed to stand at room temperature for 5–10 min. The plant pot is transferred to a tray, which is covered with a wrap to maintain the humidity. The next day, the wrap is removed. The plant is grown in that state to harvest seeds.

Subsequently, the seeds are sown on MS agar medium supplemented with appropriate antibiotics to select those individuals which have the gene of interest. Arabidopsis thaliana grown on this medium are transferred to pots and grown there. As a result, seeds of a transgenic plant into which the gene of the invention is introduced can be obtained.

Generally, introduced genes are located on the genome of the host plant in a similar manner. However, due to the difference in the locations on the genome, the expression of the introduced genes varies. This is a phenomenon called position effect. By assaying transformants by Northern blotting with a DNA fragment from the introduced gene as a probe, it is possible to select those transformants in which the introduced gene is expressed more highly.

The confirmation that the gene of interest is integrated in the transgenic plant of the invention and in the subsequent generation thereof can be made by extracting DNA from cells and tissues of those plants by conventional methods and detecting the introduced gene by PCR or Southern analysis known in the art.

5-3. Analysis of the Expression Level and Expression Site of the Gene of the Invention in Plant Tissues The expression level and expression site of the gene of the invention in a transgenic plant into which the gene is introduced can be analysed by extracting RNA from cells and tissues of the plant by conventional methods and detecting the mRNA of the introduced gene by RT-PCR or Northern analysis known in the art. Alternatively, the expression level and expression site can be analysed directly by Western blotting or the like of the product of the gene of the invention using an antibody raised against the above product.

5-4. Changes in the mRNA Levels of Various Genes in a Transgenic Plant into which the Gene of the Invention is Introduced It is possible to identify by Northern blot analysis those genes whose expression levels are believed to have been changed as a result of the action of the transcription factor of the invention in a transgenic plant into which the gene of the invention is introduced. Northern blotting can assay those genes by comparing their expression in the transgenic plant into which the gene of the invention is introduced and in plants into which the gene is not introduced.

For example, plants grown on GM agar medium or the like are given dehydration and/or low temperature stress for a specific period of time (e.g. 1 to 2 weeks). Dehydration stress may be given by pulling out the plant from the agar medium and drying it on a filter paper for 10 min to 24 hr. Low temperature stress may be given by retaining the plant at 15 to −4° C. for 10 min to 24 hr. Total RNA is prepared from control plants which did not receive any stress and plants which received dehydration and low temperature stresses. The resultant total RNA is subjected to electrophoresis. Then, genes expressing are assayed by Northern blot analysis or RT-PCR.

5-5. Evaluation of the Tolerance to Environmental Stresses of the Transgenic Plant The tolerance to environmental stresses of the transgenic plant of the invention can be evaluated by setting the plant in a pot containing a soil comprising vermiculite, perlite and the like, exposing the plant to various stresses such as dehydration, low temperature and freezing, and examining the survival of the plant. For example, tolerance to dehydration stress can be evaluated by leaving the plant without giving water for 2 to 4 weeks and then examining the survival. Tolerance to freezing stress can be evaluated by leaving the plant at −6 to −10° C. for 5 to 10 days, growing it at 20 to 25° C. for 5 to 10 days and then examining its survival ratio.

6. Antibodies against the Proteins of the Invention

In the present invention, antibodies against the proteins of the invention can also be prepared. The term "antibody" means an antibody molecule as a whole or a fragment thereof (e.g. Fab or F(ab')$_2$ fragment) which can bind to the protein of the invention that is an antigen. The antibody may be either polyclonal or monoclonal.

The antibody against the protein of the invention may be prepared by various methods. Such methods of antibody preparation are well known in the art [see, for example, Sambrook, J. et al., Molecular Cloning, Cold Spring Harbor Laboratory Press (1989)].

6-1. Preparation of Polyclonal Antibodies against the Proteins of the Invention

One of the proteins of the invention genetically engineered as described above or a fragment thereof is administered as an antigen to a mammal such as rat, mouse or rabbit. The dosage of the antigen per animal is 100 to 200 μg when an adjuvant is used. As the adjuvant, Freund's complete adjuvant (FCA), Freund's incomplete adjuvant (FIA), aluminum hydroxide adjuvant or the like may be used. Immunization is performed mainly by intravenous, subcutaneous or intraperitoneal injection. The interval of immunization is not particularly limited; immunization is carried out 1 to 5 times, preferably 5 times, at intervals of several days to several weeks, preferably at intervals of one week. Subsequently, 7 to 10 days after the final immunization, antibody titer is determined by enzyme immunoassay (EIA), radioimmunoassay (RIA) or the like. Blood is collected from the animal on the day when the maximum antibody titer is shown, to thereby obtain antiserum. When purification of antibody from the antiserum is necessary, the antibody can be purified by appropriately selecting or combining conventional methods such as ammonium sulfate salting out, ion exchange chromatography, gel filtration and affinity chromatography.

6-2. Preparation of Monoclonal Antibodies against the Proteins of the Invention (i) Recovery of Antibody-Producing Cells One of the proteins of the invention genetically engineered or a fragment thereof is administered as an antigen to a mammal such as rat, mouse or rabbit, as described above. The dosage of the antigen per animal is 100 to 200 μg when an adjuvant is used. As the adjuvant, Freund's complete adjuvant (FCA), Freund's incomplete adjuvant (FIA), aluminum hydroxide adjuvant or the like may be used. Immunization is performed mainly by intravenous, subcutaneous or intraperitoneal injection. The interval of immunization is not particularly limited; immunization is carried out 1 to 5 times, preferably 5 times, at intervals of several days to several weeks, preferably at intervals of 1 to 2 weeks. Subsequently, 7 to 10 days after the final immunization, preferably 7 days after the final immunization, antibody producing cells are collected. As antibody-producing cells, spleen cells, lymph node cells, peripheral blood cells, etc. may be enumerated. Among them, spleen cells and local lymph node cells are preferable.

(ii) Cell Fusion

In order to obtain hybridomas, cell fusion between antibody-producing cells and myeloma cells is performed. As the myeloma cells to be fused to the antibody-producing cells, a commonly available cell strain of an animal such as mouse may be used. Preferably, a cell strain to be used for this purpose is one which has drug selectivity, cannot survive in HAT selective medium (containing hypoxanthine, aminopterin and thymidine) when unfused, and can survive there only when fused to antibody-producing cells. As the myeloma cells, mouse myeloma cell strains such as P3X63-Ag.8.U1(P3U1), Sp2/0 and NS-1 may be enumerated.

Subsequently, the myeloma cells and the antibody-producing cells described above are fused. Briefly, the antibody-producing cells ($2 \times 10^7$ cells/ml) and the myeloma cells ($1 \times 10^7$ cells/ml) are mixed in equal volumes and reacted in the presence of a cell fusion promoter. As the cell fusion promoter, polyethylene glycol with a mean molecular weight of 1,500 Da may be used, for example. Alternatively, the antibody-producing cells and the myeloma cells may be fused in a commercial cell fusion apparatus utilizing electric stimulation (e.g. electroporation).

(iii) Selection and Cloning of a Hybridoma

A hybridoma of interest is selected from the cells after the cell fusion. As a method for this selection, the resultant cell suspension is appropriately diluted with fetal bovine serum-containing RPMI-1640 medium or the like and then plated on microtiter plates at a density of about 0.8 to 1 cell/well. Then, a selective medium is added to each well. Subsequently, the cells are cultured while appropriately exchanging the selective medium. As a result, about 10 days after the start of cultivation in the selective medium, the growing cells can be obtained as hybridomas.

Subsequently, screening is performed as to whether the antibody of interest is present in the culture supernatant of the grown hybridomas. The screening of hybridomas may be performed by any of conventional methods. For example, a part of the culture supernatant of a well in which a hybridoma is grown is collected and subjected to enzyme immunoassay or radioimmunoassay.

Cloning of the fused cell is performed by the limiting dilution method, for example. Finally, the hybridoma of interest which is a monoclonal antibody-producing cell is established.

(iv) Recovery of the Monoclonal Antibody

As a method for recovering the monoclonal antibody from the thus established hybridoma, the conventional cell culture method or abdominal dropsy formation method may be employed.

In the cell culture method, the hybridoma is cultured in an animal cell culture medium such as 10% fetal bovine serum-containing RPMI-1640 medium, MEM medium or a serum-free medium under conventional culture conditions (e.g. at 37° C. under 5% $CO_2$) for 7 to 14 days. Then, the monoclonal antibody is recovered from the culture supernatant.

In the abdominal dropsy formation method, about $1\times10^7$ cells of the hybridoma is administered to the abdominal cavity of an animal syngeneic to the mammal from which the myeloma cells were derived, to thereby propagate the hybridoma greatly. One to two weeks thereafter, the abdominal dropsy or serum is collected.

If purification of the antibody is necessary in the above-mentioned method of recovery, the antibody can be purified by appropriately selecting or combining conventional methods such as ammonium sulfate salting out, ion exchange chromatography, gel filtration and affinity chromatography.

Once the polyclonal or monoclonal antibody is thus obtained, the antibody may be bound to a solid carrier as a ligand to thereby prepare an affinity chromatography column. With this column, the protein of the invention can be purified from the above-mentioned source or other sources. Besides, these antibodies can also be used in Western blotting to detect the protein of the invention.

7. Determination of Stress Levels in Plants

The transcription of DREB1A gene of the invention is activated mainly by low temperature stress, and the transcription of DREB2A gene by dehydration stress and salt stress. Therefore, by determining the transcription level of the gene of the invention, it is possible to know the level of stress such as low temperature, dehydration or salt which a plant is undergoing.

In protected culture of a crop using vinyl houses or the like, the environmental arrangement cost for providing light, heat, water, soil, etc. occupies 20–80% of the production cost of the crop. Under such circumstances, if it is possible to grasp promptly whether the crop is subjected to low temperature stress, dehydration stress or salt stress, the environmental arrangement cost can be minimized to thereby reduce the production cost greatly.

The transcription level of the gene of the invention can be determined by RNA gel blot analysis or quantitative PCR, for example. As a probe to be used in RNA gel blot analysis, DREB1A gene and/or a 100–1000 bp DNA region comprising a DREB1A gene specific sequence adjacent to DREB1A gene may be used for the detection of DREB1A gene. For the detection of DREB2A gene, DREB2A gene and/or a 100–1000 bp DNA region comprising a DREB2A gene specific sequence adjacent to DREB2A gene may be used. As a primer to be used in quantitative PCR, a 17–25 bp oligonucleotide within the coding sequence of DREB1A gene or adjacent thereto which is capable of specifically amplifying DREB1A gene may be used for amplifying DREB1A gene. Likewise, a 17–25 bp oligonucleotide within the coding sequence of DREB2A gene or adjacent thereto which is capable of specifically amplifying DREB2A gene may be used for amplifying DREB2A gene.

The above-described probe or primer may be used in a kit for determining the transcription level of DREB1A or DREB2A gene.

PREFERRED EMBODIMENTS OF THE INVENTION

Hereinbelow, the present invention will be described more specifically with reference to the following Examples. However, the technical scope of the present invention is not limited to these Examples.

EXAMPLE 1

Cultivation of *Arabidopsis thaliana* Plant Bodies

*Arabidopsis thaliana* seeds obtained from LEHLE were sterilized in a solution containing 1% sodium hypochlorite and 0.02% Triton X-100 for 15 min. After rinsing with sterilized water, 40–120 seeds were sown on GM agar medium [4.6 g/L mixed salts for Murashige-Skoog medium (Nihon Pharmaceutical Co., Ltd.), 0.5 g/L MES, 30 g/L sucrose, 8 g/L agar, pH 5.7] and cultured at 22° C. under light conditions of about 1000 lux and 16 hr light 8 hr dark, to thereby obtain plant bodies.

EXAMPLE 2

Cloning of DREB1A Gene and DREB2A Gene (1) Preparation of Poly(A)$^+$ RNA

The plant bodies obtained in Example 1 were subjected to low temperature treatment at 4° C. for 24 hr, and then total RNA was prepared from them by the glyoxal method. Briefly, 3 g of *Arabidopsis thaliana* plant bodies frozen in liquid nitrogen was suspended in 100 ml of 5.5 M GTC solution (5.5 M guanidine thiocyanate, 25 mM sodium citrate, 0.5% sodium N-lauroyl sarcosinate) and solubilized quickly with a homogenizer. This homogenate was sucked into and extruded from a syringe provided with a 18-G needle repeatedly more than 10 times to thereby disrupt the DNA. Then, the homogenate was centrifuged at 4° C. at 12,000×g for 15 min to precipitate and remove the cell debris.

The resultant supernatant was overlayered on a cushion of 17 ml of CsTFA solution [a solution obtained by mixing cesium trifluoroacetate (Pharmacia), 0.25 M EDTA and sterilized water to give D=1.51] placed in an autoclaved centrifuge tube, and then ultracentrifuged in Beckmann SW28 Rotor at 15° C. at 25,000×rpm for 24 hr to precipitate total RNA.

The resultant total RNA was dissolved in 600 μl of 4 M GTC solution (obtained by diluting the above-described 5.5 M GTC solution with sterilized water to give a GTC concentration of 4 M) and precipitated with ethanol to thereby obtain total RNA.

The resultant total RNA was dissolved in 2 ml of TE/NaCl solution (1:1 mixture of TE and 1 M NaCl) and passed through an oligo-dT cellulose column [prepared by packing a Bio-Rad Econocolumn (0.6 cm in diameter) with oligo-dT cellulose (type 3) (Collaborative Research) to a height of 1.5 cm] equilibrated with TE/NaCl in advance. The solution passed through the column was fed to the column again. Subsequently, the column was washed with about 8 ml of TE/NaCl. TE was added thereto to elute and purify poly(A)$^+$ RNA. The amount of the thus obtained RNA was determined with a UV spectroscope.

(2) Synthesis of a cDNA Library

Double-stranded cDNA was synthesized with a cDNA synthesis kit (Stratagene) using 5 μg of the poly(A)$^+$ RNA obtained in (1) above. Then, the double-stranded cDNA was ligated to pAD-GAL4 plasmid (Stratagene) to thereby synthesize a cDNA library. Briefly, at first, single-stranded cDNA was synthesized in the following reaction solution according to the protocol attached to the kit.

| | |
|---|---|
| Poly (A)⁺ RNA | 5 µl (5 µg) |
| 10x 1st Strand synthesis buffer | 5 µl |
| DEPC-treated water | 34 µl |
| 40 U/µl Ribonuclease inhibitor | 1 µl |
| Nucleotide mix for 1st strand | 3 µl |
| 1.4 µg/µl Linker primer | 2 µl |
| Total | 50 µl |

To the above solution, 1.5 µl (50 U/µl) of reverse transcriptase was added and incubated at 37° C. for 1 hr to thereby synthesize single-stranded cDNA. To the resultant reaction solution containing single-stranded cDNA, the following reagents were added in the indicated order.

| | |
|---|---|
| Reaction solution containing single-stranded cDNA | 45 µl |
| 10x 2nd Strand synthesis buffer | 20 µl |
| NTP mix for 2nd strand | 6 µl |
| 1.5 U/µl RNase H | 2 µl |
| 9 U/µl DNA polymerase I | 11 µl |
| DEPC-treated water | 116 µl |
| Total | 200 µl |

The resultant reaction solution was incubated at 16° C. for 2.5 hr to thereby synthesize double-stranded cDNA.

The synthesized double-stranded cDNA was blunt-ended by incubating it with 5 units of Pfu DNA polymerase at 72° C. for 30 min. Subsequently, the resultant cDNA was subjected to phenol/chloroform extraction and ethanol precipitation. To the resultant pellet, 9 µl of EcoRI-NotI-BamHI adaptor (Takara), 1 µl of 10×ligase buffer, 1 µl of ATP and 1 µl of T4 DNA ligase (4 U/µl ) were added and incubated at 4° C. for 2 days to thereby add the adaptor to the double-stranded cDNA.

Subsequently, the cDNA having an EcoRI restriction enzyme site at both ends was ligated to the EcoRI site downstream of the GAL4 activation domain of pAD-GAL4 plasmid (Stratagene) (a cloning vector) with T4 DNA ligase to thereby synthesize a cDNA library.

(3) Preparation of Genomic DNA

Genomic DNA was prepared from the plant bodies obtained in Example 1 according to the method described by Maniatis, T. et al. [Molecular Cloning: A Laboratory Manual, pp. 187–198, Cold Spring Harbor Laboratory Press, Cold Spring Harbor, N.Y. (1982)]. Briefly, 2,000 ml of disruption buffer [0.35 M sucrose, 1 M Tris-HCl (pH 8.0), 5 mM MgCl$_2$, 50 mM KCl] was added to 50 g of *Arabidopsis thaliana* plant bodies. The mixture was disrupted in a whirling blender for 1 min 3 times to homogenize the plant bodies.

The disrupted solution was filtered to remove the cell residue. The filtrate was transferred into centrifuge tubes and centrifuged in a swing rotor at 3,000×g at 4° C. for 10 min at a low speed. The resultant supernatant was discarded. The precipitate was suspended in 30 ml of ice-cooled disruption buffer and then re-centrifuged at a low speed. The same procedures were repeated 3 times until the green precipitate turned into white.

The resultant white precipitate was suspended in 10 ml of ice-cooled TE. To this suspension, 10 ml of lysis solution (0.2 M Tris-HCl (pH 8.0), 50 mM EDTA, 2% sodium N-lauroyl sarcosinate) was added. Then, 0.1 ml of proteinase K (10 mg/ml) was added thereto to digest nuclei. The resultant digest was subjected to phenol treatment and ethanol precipitation. The DNA fiber obtained by the precipitation was recovered by centrifugation at 3,000×g for 5 min and dissolved in 1 ml of TE to thereby obtain genomic DNA.

(4) Construction of a Host Yeast for Use in Yeast One Hybrid Screening

For the cloning of a gene encoding the transcription factor (DRE-binding protein) of the invention, a host was constructed (FIG. 1). This host for cloning comprises two plasmids, one containing 4 cassettes of DRE motif-containing DNA upstream of HIS3 reporter gene and the other containing 4 cassettes of DRE motif-containing DNA upstream of lacZ reporter gene. Briefly, first, the promoter region of rd29A gene (the region from −215 to −145 based on the translation initiation site of rd29A gene) comprising DRE sequence to which the transcription factor of the invention binds to was amplified by PCR. As a sense primer, 5'-aagcttaagcttacatcagtttgaaagaaa-3' (SEQ ID NO: 11) was synthesized. As an antisense primer, 5'-aagcttaagcttgcttttggaactcatgtc-3' (SEQ ID NO: 12) was synthesized. To these primers, a HindIII restriction site was introduced to their 5' end so that PCR fragments can be ligated to a vector easily after amplification. These primers were synthesized chemically with a fully automated DNA synthesizer (Perkin-Elmer). A PCR was performed using these primers and the genomic DNA from (3) above as a template. The composition of the PCR reaction solution was as follows.

| | |
|---|---|
| Genomic DNA solution | 5 µl (100 ng) |
| Sterilized water | 37 µl |
| 10x PCR buffer [1.2 M Tris-HCl (pH 8.0), 100 mM KCl, 60 mM (NH$_4$)$_2$SO$_4$, 1% Triton X-100, 0.1 mg/ml BSA] | 5 µl |
| 50 pmol/µl Sense primer | 1 µl (50 pmol) |
| 50 pmol/µl Antisense primer | 1 µl (50 pmol) |
| KOD DNA polymerase (KOD-101, TOYOBO) | 1 µl (2.5 U) |
| Total | 50 µl |

After the above reaction solution was mixed thoroughly, 50 µl of mineral oil was overlayered on it. The PCR was performed 25 cycles, one cycle consisting of thermal denaturation at 98° C. for 15 sec, annealing at 65° C. for 2 sec and extension at 74° C. for 30 sec. After completion of the reaction, 50 µl of chloroform was added to the reaction solution, and then the resultant mixture was centrifuged at 4° C. at 15,000 rpm for 15 min. The resultant upper layer was recovered into a fresh microtube, to which 100 µl of ethanol was added and mixed well. The mixture was centrifuged at 4° C. at 15,000 rpm for 15 min to pellet the PCR product.

The resultant PCR product was digested with HindIII and then ligated to the HindIII site of vector pSK to yield a recombinant plasmid. This plasmid was transformed into *E coli*. From the transformant, plasmid DNA was prepared to determine the nucleotide sequence. By these procedures, a transformant comprising pSK with a DNA fragment containing 4 cassettes of DRE connected in the same direction was selected.

The DNA fragment containing 4 cassettes of DRE was cut out from pSK plasmid using EcoRI and HincII, and then ligated to the EcoRI-MluI site upstream of the HIS3 minimum promoter of a yeast expression vector pHISi-1 (Clontech). Likewise, the DRE-containing DNA fragment was cut out from pSK plasmid using EcoRI and HincII, and then ligated to the EcoRI-SalI site upstream of the lacZ minimum promoter of a yeast expression vector pLacZi (Clontech). The resultant two plasmids were transformed into *Saccharomyces cerevisiae* YM4271 (MATa, ura3-52, his3-200, ade2-101, lys2-801, leu2-3, 112, trp1-903) (Clontech) to thereby yield a host yeast to be used in yeast one hybrid screening (FIG. 1).

(5) Cloning of DREB1A Gene and DREB2A Gene

The host yeast prepared in (4) above was transformed with the cDNA library prepared in (2) above. The resultant yeast transformants (1.2×10⁶) were cultured and screened as described previously. As a result, two positive clones were obtained. The cDNAs of these clones were cut out from pAD-GAL4 plasmid using EcoRI and then ligated to the EcoRI site of pSK plasmid to thereby obtain pSKDREB1A and pSKDREB2A.

(6) Determination of the Nucleotide Sequences

The entire nucleotide sequences were determined on plasmids pSKDREB1A and pSKDREB2A. The plasmids used for the sequencing were prepared with an automated plasmid preparation apparatus Model PI-100 (Kurabo). For the sequencing reaction, a reaction robot CATALYST 800 (Perkin Elmer) was used. For the DNA sequencing, Perkin Elmer Sequencer Model 373A was used. As a result, it was found that the cDNA from plasmid pSKDREB1A consists of 933 bases. From the analysis of its open reading frame, it was found that the gene product encoded by DREB1A gene is a protein consisting of 216 amino acid residues with a molecular weight of about 24.2 kDa. This protein is encoded by the nucleotide sequence from position 119 (adenine) to position 766 (thymine) of SEQ ID NO: 1. On the other hand, it was found that the cDNA from plasmid pSKDREB2A consists of 1437 bases. From the analysis of its open reading frame, it was found that the gene product encoded by DREB2A gene is a protein consisting of 335 amino acid residues with a molecular weight of about 37.7 kDa.

(7) Isolation of Genes Encoding Homologues to DREB1A or DREB2A Protein

Genes encoding homologues to the protein encoded by DREB1A or DREB2A gene were isolated. Briefly, genes encoding such homologues were isolated from *Arabidopsis thaliana* λgt11 cDNA library using as a probe the double-stranded cDNA fragment comprising DREB1A or DREB2A gene obtained in (5) above according to the method described by Sambrook, J. et al., Molecular Cloning: A Laboratory Manual 2nd Ed., Cold Spring Harbor Laboratory Press, N.Y. (1989)]. As genes encoding homologues to DREB1A protein, DREB1B gene and DREB1C gene were obtained; as a gene encoding a homologue to DREB2A protein, DREB2B gene was obtained. As a result of DNA sequencing, it was found that DREB1B gene (SEQ ID NO: 5) is identical with CBF1 [Stockinger, E. J. et al., Proc. Natl. Acad. Sci. USA 94:1035–1040 (1997)], but DREB1C gene (SEQ ID NO: 7) and DREB2B gene (SEQ ID NO: 9) were found to be novel.

From the analysis of the open reading frame of DREB1C gene, it was found that the gene product encoded by this gene is a protein consisting of 216 amino acid residues with a molecular weight of about 24.3 kDa (SEQ ID NO: 8). Also, it was found that the gene product encoded by DREB2B gene is a protein consisting of 330 amino acid residues with a molecular weight of about 37.1 kDa (SEQ ID NO: 10). SEQ ID NO:6 is the amino acid sequence of DREB1B protein.

EXAMPLE 3

Analysis of the DRE-Binding Ability of DREB1A and DREB2A Proteins

The ability of DREB1A and DREB2A proteins to bind to DRE was analyzed by preparing a fusion protein composed of glutathione-S-transferase (GST) and DREB1A or DREB2A protein using *E. coli* and then performing a gel shift assay. Briefly, the 429 bp DNA fragment located from position 119 to position 547 of the nucleotide sequence of DREB1A cDNA or the 500 bp DNA fragment located from position 167 to position 666 of the nucleotide sequence of DREB2A cDNA was amplified by PCR. Then, the amplified fragment was ligated to the EcoRI-SalI site of plasmid pGEX-4T-1 (Pharmacia). After the introduction of this plasmid into *E. coli* JM109, the resultant transformant was cultured in 200 ml of 2×YT medium (Molecular Cloning, (1982) Cold Spring Harbor Laboratory Press). To this culture, 1 mM isopropyl β-D-thiogalactoside which activates the promoter of plasmid pGEX-4T-1 was added to thereby induce the synthesis of a fusion protein of DREB1A (or DREB2A) and GST.

Figure 2:
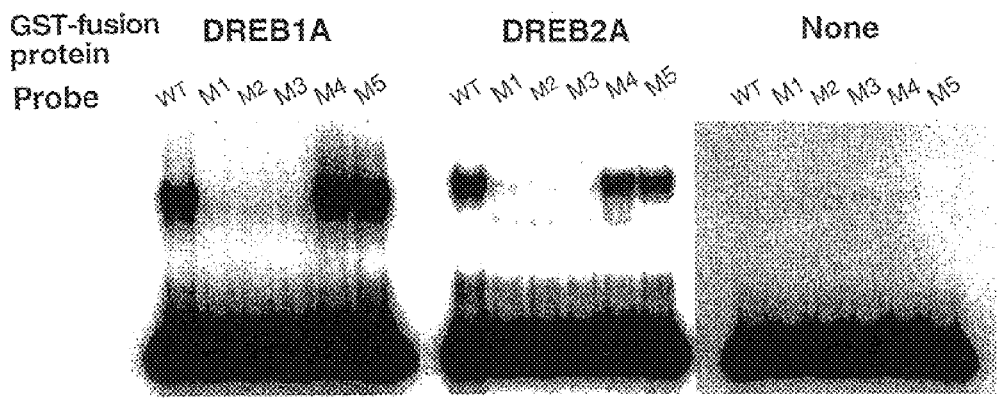
FIG. 2A shows DRE (dehydration responsive element) region.
FIG. 2B presents photographs showing the results of gel shift assay on the DRE-binding property of DREB1A and DREB2A proteins.

*E. coli* in which the fusion protein had been induced was lysed in 13 ml of buffer (10 mM Tris-HCl, 0.1 mM DTT, 0.1 mM phenylmethylsulfonyl fluoride). Then, 1% Triton X-100 and 1 mM EDTA were added thereto. After the cells were disrupted by sonication, the disrupted material was centrifuged at 22,000 g for 20 min. Then, the fusion protein was purified with glutathione-Sepharose (Pharmacia). The resultant fusion protein was mixed with the DRE-containing 71 bp DNA fragment labelled with $^{32}$P as a probe, and incubated at room temperature for 20 min. This mixture was electrophoresed using 6% acryl amide gel containing 0.25× Tris-borate-EDTA at 100 V for 2 hr. As a result of this gel shift analysis, those bands which migrated behind were detected. When a DNA fragment containing a varied DRE sequence was used, such bands were not detected. Thus, it became evident that DREB1A and DREB2A proteins specifically bound to DRE sequence (FIG. 2).

EXAMPLE 4

Analysis of the Ability of DREB1A and DREB2A Proteins to Activate the Transcription of Genes Located Downstream of DRE In order to examine whether DREB1A and DREB2A proteins are able to trans-activate DRE-dependent transcription in plant cells, a trans-activation experiment was conducted using a protoplast system prepared from *Arabidopsis thaliana* leaves. Briefly, the cDNA of DREB1A or DREB2A was ligated to a pBI221 plasmid containing CaMV35S promoter to thereby construct an effector plasmid.

Figure 3:
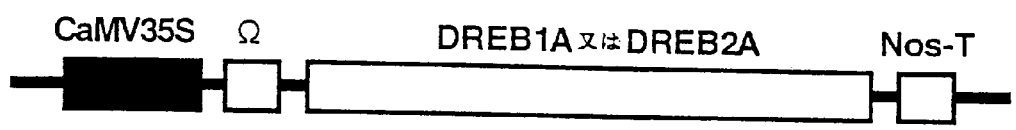
FIG. 3A depicts construction of an Effector Plasmid and a Reportor Plasmid, respectively.
FIG. 3B presents diagrams showing the transcription activating ability of DREB 1A and DREB2A proteins.
Figure 3:
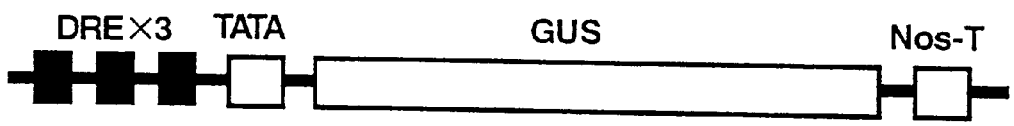
Figure 3:
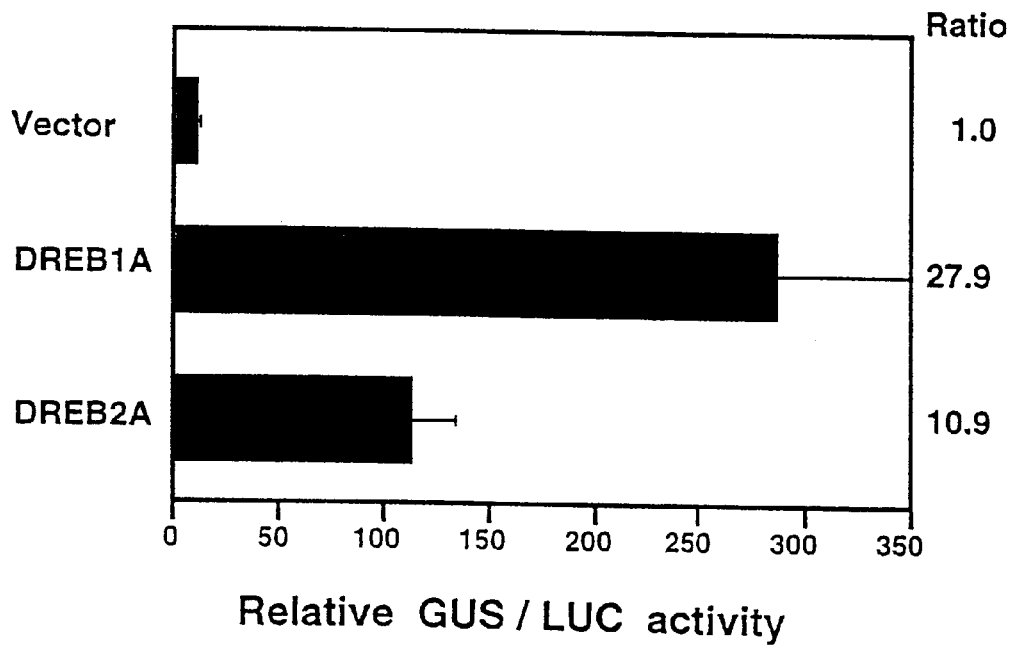

On the other hand, 3 cassettes of the DRE-containing 71 base DNA region were connected tandemly to prepare a DNA fragment, which was ligated upstream to the minimum TATA promoter located upstream of β-glucuronidase (GUS) gene in a plasmid derived from pBI221 plasmid to construct a reporter plasmid. Subsequently, these two plasmids were introduced into protoplasts from *Arabidopsis thaliana* and then GUS activity was determined. When DREB1A or DREB2A protein was expressed simultaneously, GUS activity increased. This shows that DREB1A and DREB2A proteins are transcription factors which activate transcription through DRE sequence (FIG. 3).

EXAMPLE 5

(1) Construction of a Plant Plasmid

Figure 4:
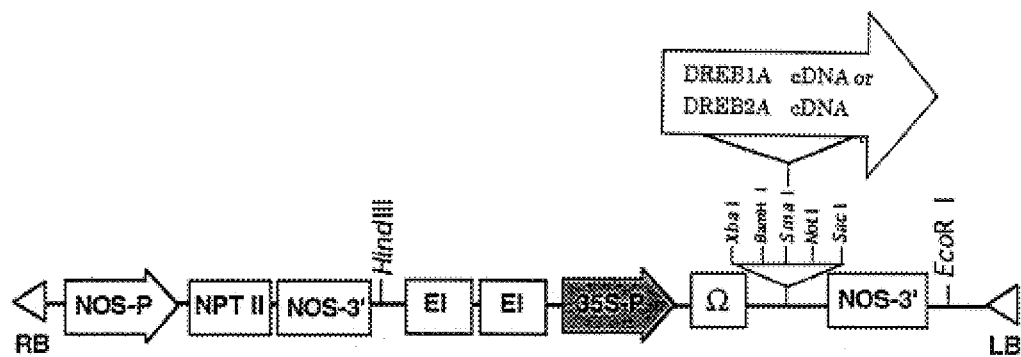
FIG. 4 is a diagram showing the structure of a recombinant plasmid to be introduced into a plant.

Plasmid pSKDREB1A (10 μg) obtained as described above was digested with EcoRV (20 U) and SmaI (20 U) in a buffer containing 10 mM Tris-HCl (pH 7.5), 10 mM $MgCl_2$, 1 mM dithiothreitol (DTT) and 100 mM NaCl at 37° C. for 2 hr to thereby obtain a DNA fragment of about 0.9 kb containing DREB1A gene. On the other hand, plasmid pBI2113Not (10 μg) containing promoter DNA was digested with SmaI in a buffer containing 10 mM Tris-HCl (pH 7.5), 10 MM $MgCl_2$, 1 mM DTT and 100 mM NaCl at 37° C. for 2 hr. The 0.9 kb DNA fragment containing DREB1A gene obtained by digestion and the digested pBI2113Not were treated with T4 DNA ligase (2 U) in a buffer [66 mM Tris-HCl (pH 7.6), 6.6 mM $MgCl_2$, 10 mM DTT, 0.1 mM ATP] at 15° C. for 16 hr. The resultant DNA was transformed into E. coli JM109, from which plasmid pBI35S:DREB1A was obtained. With respect to the direction of DREB1A gene, those plasmids in which this gene was ligated in the sense direction were selected by determining the nucleotide sequence at the junction site of plasmid pBI35S:DREB1A. Plasmid pBI2113Not mentioned above is a plasmid prepared by digesting pBI2113[Plant Cell Physiology 37:49–59 (1996)] with SmaI and SacI to remove the coding region of GUS gene and ligating a SmaI-NotI-Sac polylinker to the resultant plasmid. The plant plasmid pBI35S:DREB1A prepared as described above was transformed into E. coli DH5a (FIG. 4).

Briefly, the plant plasmid pBI35S:DREB1A, E. coli DH5α, helper plasmid pRK2013-containing E. coli HB101 and Agrobacterium C58 were mixed and cultured on LB agar medium at 28° C. for 24 hr. Grown colonies were scraped off and suspended in 1 ml of LB medium. This suspension (10 ml) was plated on LB agar medium containing 100 μg/ml rifampicin and 20μg/ml kanamycin and cultured at 28° C. for 2 days to thereby obtain a zygote Agrobacterium C58 (pBI35S:DREB1A).

(2) Gene Transfer into Arabidopsis thaliana by Agrobacterium Infection.

The resultant Agrobacterium was cultured in 10 ml of LB medium containing 100 μg/ml rifampicin and 20 μg/ml kanamycin at 28° C. for 24 hr. Further, this culture fluid was added to 500 ml of LB medium and cultured for another 24 hr. The resultant culture fluid was centrifuged to remove the medium, and the cell pellet was suspended in 250 ml of LB medium.

On the other hand, 4 to 5 Arabidopsis thaliana plant bodies were grown in 9 cm pots containing soil composed of vermiculite and perlite (50:50) for 6 weeks. Then, the plant body was directly dipped in the LB culture fluid containing the Agrobacterium bearing plasmid pBI35S:DREB1A and placed in a desiccator, which was sucked with a vacuum pump to reduce the pressure to 650 mmHg and then left for 10 min. Subsequently, the plant pot was transferred to a tray and covered with a wrap to maintain the humidity. The next day, the wrap was removed. Thereafter, the plant was grown uncovered to thereby obtain seeds. After sterilization in an aqueous solution of sodium hypochlorite, the seeds were sown on an agar medium for selection (MS medium supplemented with 100 μg/ml vancomycin and 30 μg/ml kanamycin). Arabidopsis thaliana seedlings grown on this medium were transplanted to pots and grown there to obtain seeds of the transformed plant.

Figure 5:
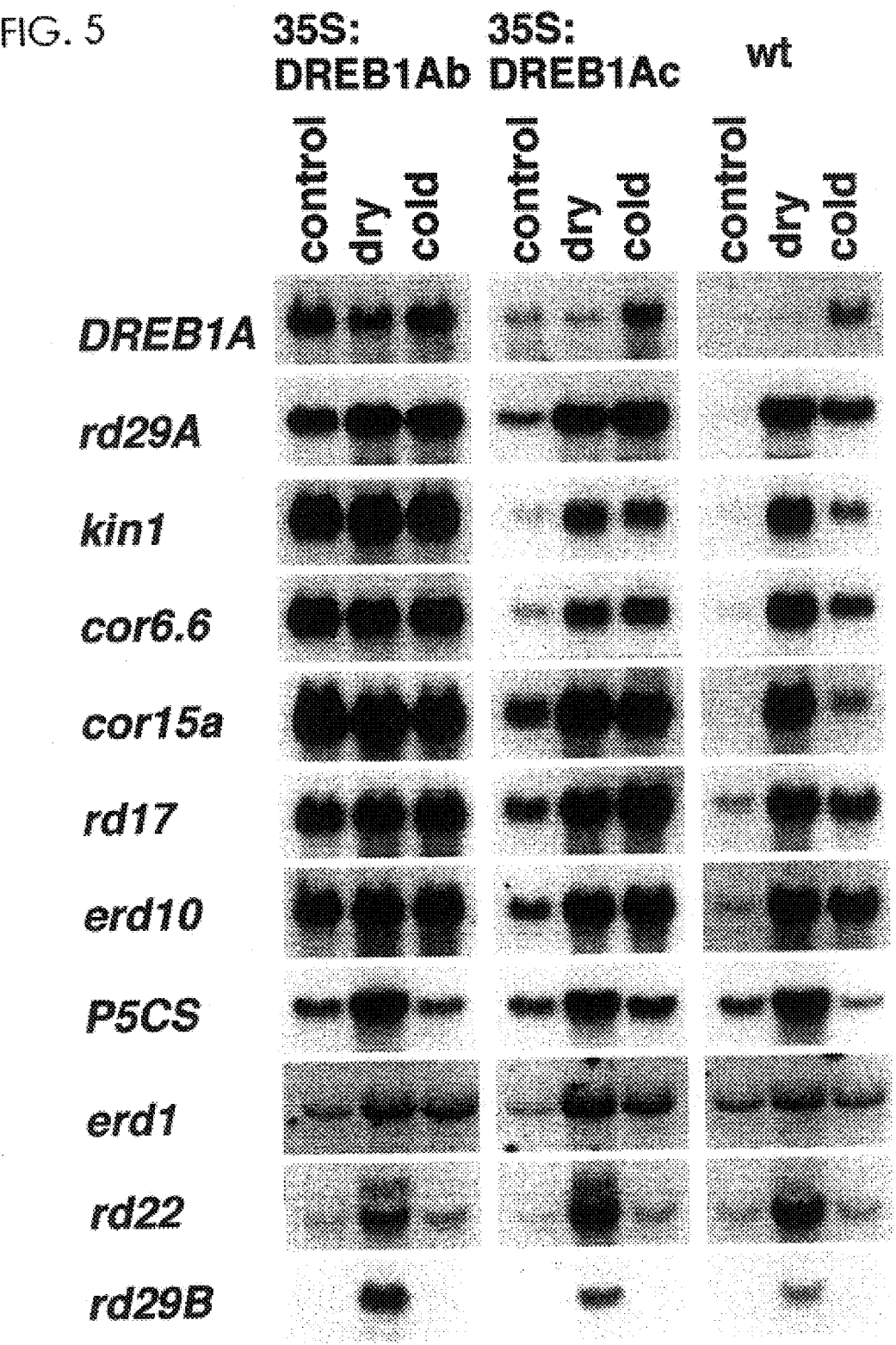
FIG. 5 presents photographs showing transcription levels of individual genes in DREB1A gene-introduced plants when stress is given.

(3) Identification of Genes Whose Expression Has Been Altered by the Introduced Gene and the Transcription Factor Encoded by the Gene Genes whose expression is considered to have been altered by the introduced gene DREB1A and the transcription factor encoded by this gene in the transformed plant were identified by Northern blot analysis. In this analysis, transcriptional activation of DREB1A, rd29A, kin1, cor6.6, cor15a, rd17, erd10, P5CS, erd1, rd22 and rd29B genes were investigated. Transformed and wild type Arabidopsis thaliana plants were used for comparing the expression of the above genes. Two grams of plant bodies grown on GM agar medium for 3 weeks were exposed to dehydration stress and low temperature stress. Dehydration stress was given by pulling out the plant from the agar medium and drying it on a filter paper for 5 hr. Low temperature stress was given by retaining the plant at 4° C. for 5 hr. Total RNA was prepared separately from control plants which was given no stress and plants which were given dehydration and low temperature stresses. The resultant total RNA was subjected to electrophoresis. Then, expressing genes were assayed by Northern blot analysis. Generally, introduced genes are located on the genome of a transformed plant in a similar manner. However, due to the difference in the locations on the genome, the expression of the introduced genes varies. This is a phenomenon called position effect. By assaying transformants by Northern blotting with a DNA fragment from the introduced gene as a probe, those transformants in which the introduced gene was expressed more highly could be selected. Also, by using a DNA fragment of the gene involved in stress tolerance as a probe, stress tolerance genes which exhibit changes when DREB1A gene is introduced could be identified (FIG. 5).

EXAMPLE 6

Expression of Dehydration/Freezing Tolerance

Dehydration/freezing tolerance was investigated on Arabidopsis thaliana transformant comprising DREB1A gene which had been grown in 9 cm pots containing soil composed of vermiculite and perlite (50:50) for 3 weeks. As a control, Arabidopsis thaliana transformed with pBI121 not containing DREB1A gene was used. As to dehydration tolerance, water supply was stopped for 2 weeks and then plant survival was examined. As to freezing tolerance, the plant was maintained at −6° C. for 2 days and then grown at 22° C. for 5 days. Thereafter, its survival ratio was examined.

Figure 6:
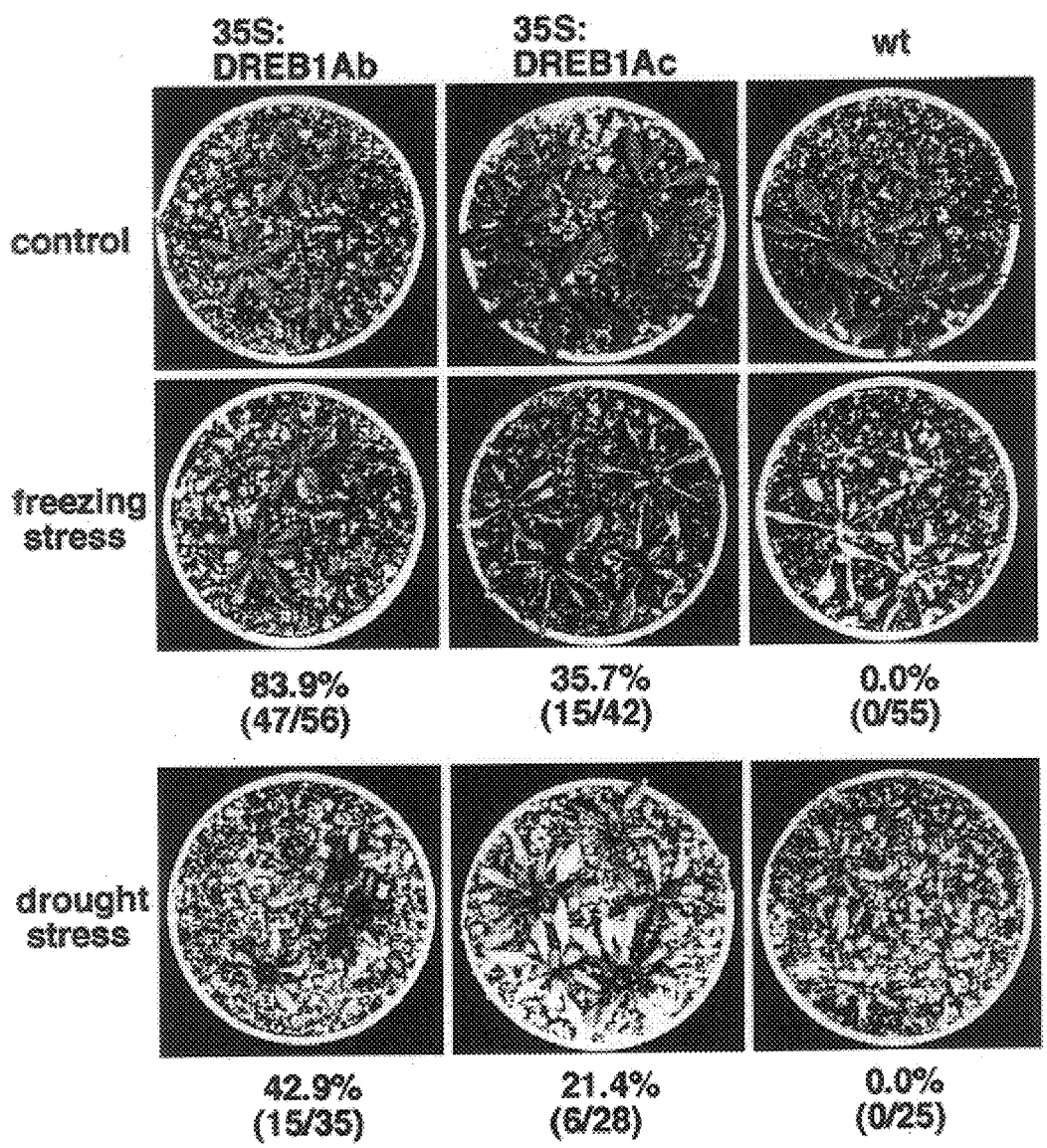
FIG. 6 presents photographs showing the growth of DREB2A gene-introduced plants when freezing stress or dehydration stress is given.

As a result, all the control plants were withered but the transgenic plants into which DREB1A gene is introduced exhibited a high survival ratio (FIG. 6).

This specification includes part or all of the contents as disclosed in the specification and/or drawings of Japanese Patent Application No. 10-228457, which is a priority document of the present application.

All publications, patents and patent applications cited herein are incorporated herein by reference in their entirety.

EFFECT OF THE INVENTION

According to the present invention, a protein which binds to DRE to activate the transcription of genes located downstream of the DRE, a gene encoding the protein, a recombinant vector comprising the gene, a transformant comprising the recombinant vector, a transgenic plant comprising the gene, and a method for producing the gene using the transformant are provided. The present invention is useful for creating a stress tolerant plant.

What is claimed is:

1. An isolated transcription factor gene coding for a protein consisting of the amino acid sequence as shown in SEQ ID NO:2.

2. An isolated gene comprising a DNA consisting of the nucleotide sequence as shown in SEQ ID NO: 1.

3. The gene according to claim 1, wherein the protein regulates the transcription of genes located downstream of a stress responsive element, wherein said stress is dehydration stress, low temperature stress or salt stress.

4. A recombinant vector comprising the gene according to claim 1.

5. A host cell transformant transformed with the recombinant vector according to claim 4.

6. A transgenic plant transformed with the gene according to claim 1.

* * * * *

UNITED STATES PATENT AND TRADEMARK OFFICE
CERTIFICATE OF CORRECTION

PATENT NO.    : 6,495,742 B1
DATED         : December 17, 2002
INVENTOR(S)   : Shinozaki et al.

It is certified that error appears in the above-identified patent and that said Letters Patent is hereby corrected as shown below:

<u>Title page,</u>
Item [73], Assignee, please replace "Tusukuba" with -- Tsukuba --

Signed and Sealed this

Third Day of June, 2003

JAMES E. ROGAN
*Director of the United States Patent and Trademark Office*

SEQUENCE LISTING

<160> NUMBER OF SEQ ID NOS: 12

<210> SEQ ID NO 1
<211> LENGTH: 933
<212> TYPE: DNA
<213> ORGANISM: Arabidopsis thaliana
<220> FEATURE:
<221> NAME/KEY: CDS
<222> LOCATION: (119)..(766)

<400> SEQUENCE: 1

```
cctgaactag aacagaaaga gagagaaact attatttcag caaaccatac caacaaaaaa      60
gacagagatc ttttagttac cttatccagt ttcttgaaac agagtactct tctgatca        118 atg aac tca ttt tct gct ttt tct gaa atg ttt ggc tcc gat tac gag        166
Met Asn Ser Phe Ser Ala Phe Ser Glu Met Phe Gly Ser Asp Tyr Glu
 1               5                  10                  15 tct tcg gtt tcc tca ggc ggt gat tat att ccg acg ctt gcg agc agc        214
Ser Ser Val Ser Ser Gly Gly Asp Tyr Ile Pro Thr Leu Ala Ser Ser
             20                  25                  30 tgc ccc aag aaa ccg gcg ggt cgt aag aag ttt cgt gag act cgt cac        262
Cys Pro Lys Lys Pro Ala Gly Arg Lys Lys Phe Arg Glu Thr Arg His
         35                  40                  45 cca ata tac aga gga gtt cgt cgg aga aac tcc ggt aag tgg gtt tgt        310
Pro Ile Tyr Arg Gly Val Arg Arg Arg Asn Ser Gly Lys Trp Val Cys
     50                  55                  60 gag gtt aga gaa cca aac aag aaa aca agg att tgg ctc gga aca ttt        358
Glu Val Arg Glu Pro Asn Lys Lys Thr Arg Ile Trp Leu Gly Thr Phe
 65                  70                  75                  80 caa acc gct gag atg gca gct cga gct cac gac gtt gcc gct tta gcc        406
Gln Thr Ala Glu Met Ala Ala Arg Ala His Asp Val Ala Ala Leu Ala
                 85                  90                  95 ctt cgt ggc cga tca gcc tgt ctc aat ttc gct gac tcg gct tgg aga        454
Leu Arg Gly Arg Ser Ala Cys Leu Asn Phe Ala Asp Ser Ala Trp Arg
            100                 105                 110 ctc cga atc ccg gaa tca act tgc gct aag gac atc caa aag gcg gcg        502
Leu Arg Ile Pro Glu Ser Thr Cys Ala Lys Asp Ile Gln Lys Ala Ala
        115                 120                 125 gct gaa gct gcg ttg gcg ttt cag gat gag atg tgt gat gcg acg acg        550
Ala Glu Ala Ala Leu Ala Phe Gln Asp Glu Met Cys Asp Ala Thr Thr
    130                 135                 140 gat cat ggc ttc gac atg gag gag acg ttg gtg gag gct att tac acg        598
Asp His Gly Phe Asp Met Glu Glu Thr Leu Val Glu Ala Ile Tyr Thr
145                 150                 155                 160 gcg gaa cag agc gaa aat gcg ttt tat atg cac gat gag gcg atg ttt        646
Ala Glu Gln Ser Glu Asn Ala Phe Tyr Met His Asp Glu Ala Met Phe
                165                 170                 175 gag atg ccg agt ttg ttg gct aat atg gca gaa ggg atg ctt ttg ccg        694
Glu Met Pro Ser Leu Leu Ala Asn Met Ala Glu Gly Met Leu Leu Pro
            180                 185                 190 ctt ccg tcc gta cag tgg aat cat aat cat gaa gtc gac ggc gat gat        742
Leu Pro Ser Val Gln Trp Asn His Asn His Glu Val Asp Gly Asp Asp
        195                 200                 205 gac gac gta tcg tta tgg agt tat taaaactcag attattattt ccatttttag       796
Asp Asp Val Ser Leu Trp Ser Tyr
    210                 215 tacgatactt tttattttat tattattttt agatcctttt ttagaatgga atcttcatta     856
tgtttgtaaa actgagaaac gagtgtaaat taaattgatt cagtttcagt ataaaaaaaa     916
```
aaaaaaaaaa aaaaaaa                                                              933

<210> SEQ ID NO 2
<211> LENGTH: 216
<212> TYPE: PRT
<213> ORGANISM: Arabidopsis thaliana

<400> SEQUENCE: 2

Met Asn Ser Phe Ser Ala Phe Ser Glu Met Phe Gly Ser Asp Tyr Glu
 1               5                  10                  15

Ser Ser Val Ser Ser Gly Gly Asp Tyr Ile Pro Thr Leu Ala Ser Ser
            20                  25                  30

Cys Pro Lys Lys Pro Ala Gly Arg Lys Lys Phe Arg Glu Thr Arg His
        35                  40                  45

Pro Ile Tyr Arg Gly Val Arg Arg Asn Ser Gly Lys Trp Val Cys
    50                  55                  60

Glu Val Arg Glu Pro Asn Lys Lys Thr Arg Ile Trp Leu Gly Thr Phe
 65                  70                  75                  80

Gln Thr Ala Glu Met Ala Ala Arg Ala His Asp Val Ala Ala Leu Ala
                85                  90                  95

Leu Arg Gly Arg Ser Ala Cys Leu Asn Phe Ala Asp Ser Ala Trp Arg
            100                 105                 110

Leu Arg Ile Pro Glu Ser Thr Cys Ala Lys Asp Ile Gln Lys Ala Ala
        115                 120                 125

Ala Glu Ala Ala Leu Ala Phe Gln Asp Glu Met Cys Asp Ala Thr Thr
    130                 135                 140

Asp His Gly Phe Asp Met Glu Glu Thr Leu Val Glu Ala Ile Tyr Thr
145                 150                 155                 160

Ala Glu Gln Ser Glu Asn Ala Phe Tyr Met His Asp Glu Ala Met Phe
                165                 170                 175

Glu Met Pro Ser Leu Leu Ala Asn Met Ala Gly Met Leu Leu Pro
            180                 185                 190

Leu Pro Ser Val Gln Trp Asn His Asn His Glu Val Asp Gly Asp Asp
        195                 200                 205

Asp Asp Val Ser Leu Trp Ser Tyr
    210                 215

<210> SEQ ID NO 3
<211> LENGTH: 1437
<212> TYPE: DNA
<213> ORGANISM: Arabidopsis thaliana
<220> FEATURE:
<221> NAME/KEY: CDS
<222> LOCATION: (167)..(1171)

<400> SEQUENCE: 3
gctgtctgat aaaagaaga ggaaaactcg aaaaagctac acacaagaag aagaagaaaa      60
gatacgagca agaagactaa acacgaaagc gatttatcaa ctcgaaggaa gagactttga    120
ttttcaaatt tcgtcccta tagattgtgt tgtttctggg aaggag atg gca gtt        175
                                                Met Ala Val
                                                 1 tat gat cag agt gga gat aga aac aga aca caa att gat aca tcg agg      223
Tyr Asp Gln Ser Gly Asp Arg Asn Arg Thr Gln Ile Asp Thr Ser Arg
    5                  10                  15 aaa agg aaa tct aga agt aga ggt gac ggt act act gtg gct gag aga      271
Lys Arg Lys Ser Arg Ser Arg Gly Asp Gly Thr Thr Val Ala Glu Arg
 20                  25                  30                  35

-continued

| | | |
|---|---|---|
| tta aag aga tgg aaa gag tat aac gag acc gta gaa gaa gtt tct acc<br>Leu Lys Arg Trp Lys Glu Tyr Asn Glu Thr Val Glu Glu Val Ser Thr<br>                    40                        45                        50 | 319 |
| aag aag agg aaa gta cct gcg aaa ggg tcg aag aag ggt tgt atg aaa<br>Lys Lys Arg Lys Val Pro Ala Lys Gly Ser Lys Lys Gly Cys Met Lys<br>                    55                        60                        65 | 367 |
| ggt aaa gga gga cca gag aat agc cga tgt agt ttc aga gga gtt agg<br>Gly Lys Gly Gly Pro Glu Asn Ser Arg Cys Ser Phe Arg Gly Val Arg<br>                    70                        75                        80 | 415 |
| caa agg att tgg ggt aaa tgg gtt gct gag atc aga gag cct aat cga<br>Gln Arg Ile Trp Gly Lys Trp Val Ala Glu Ile Arg Glu Pro Asn Arg<br>85                      90                        95 | 463 |
| ggt agc agg ctt tgg ctt ggt act ttc cct act gct caa gaa gct gct<br>Gly Ser Arg Leu Trp Leu Gly Thr Phe Pro Thr Ala Gln Glu Ala Ala<br>100                  105                   110                  115 | 511 |
| tct gct tat gat gag gct gct aaa gct atg tat ggt cct ttg gct cgt<br>Ser Ala Tyr Asp Glu Ala Ala Lys Ala Met Tyr Gly Pro Leu Ala Arg<br>                    120                   125                  130 | 559 |
| ctt aat ttc cct cgg tct gat gcg tct gag gtt acg agt acc tca agt<br>Leu Asn Phe Pro Arg Ser Asp Ala Ser Glu Val Thr Ser Thr Ser Ser<br>                  135                   140                  145 | 607 |
| cag tct gag gtg tgt act gtt gag act cct ggt tgt gtt cat gtg aaa<br>Gln Ser Glu Val Cys Thr Val Glu Thr Pro Gly Cys Val His Val Lys<br>                    150                   155                  160 | 655 |
| aca gag gat cca gat tgt gaa tct aaa ccc ttc tcc ggt gga gtg gag<br>Thr Glu Asp Pro Asp Cys Glu Ser Lys Pro Phe Ser Gly Gly Val Glu<br>165                  170                   175 | 703 |
| ccg atg tat tgt ctg gag aat ggt gcg gaa gag atg aag aga ggt gtt<br>Pro Met Tyr Cys Leu Glu Asn Gly Ala Glu Glu Met Lys Arg Gly Val<br>180                  185                   190                  195 | 751 |
| aaa gcg gat aag cat tgg ctg agc gag ttt gaa cat aac tat tgg agt<br>Lys Ala Asp Lys His Trp Leu Ser Glu Phe Glu His Asn Tyr Trp Ser<br>                    200                   205                  210 | 799 |
| gat att ctg aaa gag aaa gag aaa cag aag gag caa ggg att gta gaa<br>Asp Ile Leu Lys Glu Lys Glu Lys Gln Lys Glu Gln Gly Ile Val Glu<br>                  215                   220                  225 | 847 |
| acc tgt cag caa caa cag cag gat tcg cta tct gtt gca gac tat ggt<br>Thr Cys Gln Gln Gln Gln Asp Ser Leu Ser Val Ala Asp Tyr Gly<br>              230                   235                  240 | 895 |
| tgg ccc aat gat gtg gat cag agt cac ttg gat tct tca gac atg ttt<br>Trp Pro Asn Asp Val Asp Gln Ser His Leu Asp Ser Ser Asp Met Phe<br>    245                   250                   255 | 943 |
| gat gtc gat gag ctt cta cgt gac cta aat ggc gac gat gtg ttt gca<br>Asp Val Asp Glu Leu Leu Arg Asp Leu Asn Gly Asp Asp Val Phe Ala<br>260                  265                   270                  275 | 991 |
| ggc tta aat cag gac cgg tac ccg ggg aac agt gtt gcc aac ggt tca<br>Gly Leu Asn Gln Asp Arg Tyr Pro Gly Asn Ser Val Ala Asn Gly Ser<br>                  280                   285                  290 | 1039 |
| tac agg ccc gag agt caa caa agt ggt ttt gat ccg cta caa agc ctc<br>Tyr Arg Pro Glu Ser Gln Gln Ser Gly Phe Asp Pro Leu Gln Ser Leu<br>                    295                   300                  305 | 1087 |
| aac tac gga ata cct ccg ttt cag ctc gag gga aag gat ggt aat gga<br>Asn Tyr Gly Ile Pro Pro Phe Gln Leu Glu Gly Lys Asp Gly Asn Gly<br>              310                   315                  320 | 1135 |
| ttc ttc gac gac ttg agt tac ttg gat ctg gag aac taaacaaaac<br>Phe Phe Asp Asp Leu Ser Tyr Leu Asp Leu Glu Asn<br>325                  330                   335 | 1181 |
| aatatgaagc tttttggatt tgatatttgc cttaatccca caacgactgt tgattctcta | 1241 |
| tccgagtttt agtgatatag agaactacag aacacgtttt ttcttgttat aaaggtgaac | 1301 |

```
tgtatatatc gaaacagtga tatgacaata gagaagacaa ctatagtttg ttagtctgct      1361
tctcttaagt tgttctttag atatgtttta tgttttgtaa caacaggaat gaataataca      1421
cacttgtaaa aaaaaa                                                      1437
```

<210> SEQ ID NO 4
<211> LENGTH: 335
<212> TYPE: PRT
<213> ORGANISM: Arabidopsis thaliana

<400> SEQUENCE: 4

```
Met Ala Val Tyr Asp Gln Ser Gly Asp Arg Asn Arg Thr Gln Ile Asp
 1               5                  10                  15

Thr Ser Arg Lys Arg Lys Ser Arg Ser Arg Gly Asp Gly Thr Thr Val
             20                  25                  30

Ala Glu Arg Leu Lys Arg Trp Lys Glu Tyr Asn Glu Thr Val Glu Glu
         35                  40                  45

Val Ser Thr Lys Lys Arg Lys Val Pro Ala Lys Gly Ser Lys Lys Gly
     50                  55                  60

Cys Met Lys Gly Lys Gly Gly Pro Glu Asn Ser Arg Cys Ser Phe Arg
 65                  70                  75                  80

Gly Val Arg Gln Arg Ile Trp Gly Lys Trp Val Ala Glu Ile Arg Glu
                 85                  90                  95

Pro Asn Arg Gly Ser Arg Leu Trp Leu Gly Thr Phe Pro Thr Ala Gln
            100                 105                 110

Glu Ala Ala Ser Ala Tyr Asp Glu Ala Ala Lys Ala Met Tyr Gly Pro
        115                 120                 125

Leu Ala Arg Leu Asn Phe Pro Arg Ser Asp Ala Ser Glu Val Thr Ser
    130                 135                 140

Thr Ser Ser Gln Ser Glu Val Cys Thr Val Glu Thr Pro Gly Cys Val
145                 150                 155                 160

His Val Lys Thr Glu Asp Pro Asp Cys Glu Ser Lys Pro Phe Ser Gly
                165                 170                 175

Gly Val Glu Pro Met Tyr Cys Leu Glu Asn Gly Ala Glu Glu Met Lys
            180                 185                 190

Arg Gly Val Lys Ala Asp Lys His Trp Leu Ser Glu Phe Glu His Asn
        195                 200                 205

Tyr Trp Ser Asp Ile Leu Lys Glu Lys Glu Lys Gln Lys Glu Gln Gly
    210                 215                 220

Ile Val Glu Thr Cys Gln Gln Gln Gln Asp Ser Leu Ser Val Ala
225                 230                 235                 240

Asp Tyr Gly Trp Pro Asn Asp Val Asp Gln Ser His Leu Asp Ser Ser
                245                 250                 255

Asp Met Phe Asp Val Asp Glu Leu Leu Arg Asp Leu Asn Gly Asp Asp
            260                 265                 270

Val Phe Ala Gly Leu Asn Gln Asp Arg Tyr Pro Gly Asn Ser Val Ala
        275                 280                 285

Asn Gly Ser Tyr Arg Pro Glu Ser Gln Gln Ser Gly Phe Asp Pro Leu
    290                 295                 300

Gln Ser Leu Asn Tyr Gly Ile Pro Pro Phe Gln Leu Glu Gly Lys Asp
305                 310                 315                 320

Gly Asn Gly Phe Phe Asp Asp Leu Ser Tyr Leu Asp Leu Glu Asn
                325                 330                 335
```

<210> SEQ ID NO 5
<211> LENGTH: 937
<212> TYPE: DNA
<213> ORGANISM: Arabidopsis thaliana
<220> FEATURE:
<221> NAME/KEY: CDS
<222> LOCATION: (164)..(802)

<400> SEQUENCE: 5

| | |
|---|---:|
| cttgaaaaag aatctacctg aaaagaaaaa aagagagag agatataaat agctttacca | 60 |
| agacagatat actatctttt attaatccaa aaagactgag aactctagta actacgtact | 120 |
| acttaaacct tatccagttt cttgaaacag agtactctga tca atg aac tca ttt<br>                                                                                                                                                   Met Asn Ser Phe<br>                                                                                                                                                  1 | 175 |
| tca gct ttt tct gaa atg ttt ggc tcc gat tac gag cct caa ggc gga<br>Ser Ala Phe Ser Glu Met Phe Gly Ser Asp Tyr Glu Pro Gln Gly Gly<br> 5                       10                   15                    20 | 223 |
| gat tat tgt ccg acg ttg gcc acg agt tgt ccg aag aaa ccg gcg ggc<br>Asp Tyr Cys Pro Thr Leu Ala Thr Ser Cys Pro Lys Lys Pro Ala Gly<br>                    25                   30                    35 | 271 |
| cgt aag aag ttt cgt gag act cgt cac cca att tac aga gga gtt cgt<br>Arg Lys Lys Phe Arg Glu Thr Arg His Pro Ile Tyr Arg Gly Val Arg<br>              40                   45                    50 | 319 |
| caa aga aac tcc ggt aag tgg gtt tct gaa gtg aga gag cca aac aag<br>Gln Arg Asn Ser Gly Lys Trp Val Ser Glu Val Arg Glu Pro Asn Lys<br>     55                   60                   65 | 367 |
| aaa acc agg att tgg ctc ggg act ttc caa acc gct gag atg gca gct<br>Lys Thr Arg Ile Trp Leu Gly Thr Phe Gln Thr Ala Glu Met Ala Ala<br> 70                        75                   80 | 415 |
| cgt gct cac gac gtc gct gca tta gcc ctc cgt ggc cga tca gca tgt<br>Arg Ala His Asp Val Ala Ala Leu Ala Leu Arg Gly Arg Ser Ala Cys<br> 85                       90                   95               100 | 463 |
| ctc aac ttc gct gac tcg gct tgg cgg cta cga atc ccg gag tca aca<br>Leu Asn Phe Ala Asp Ser Ala Trp Arg Leu Arg Ile Pro Glu Ser Thr<br>                     105                  110                 115 | 511 |
| tgc gcc aag gat atc caa aaa gcg gct gct gaa gcg gcg ttg gct ttt<br>Cys Ala Lys Asp Ile Gln Lys Ala Ala Ala Glu Ala Ala Leu Ala Phe<br>              120                   125                  130 | 559 |
| caa gat gag acg tgt gat acg acg acc acg aat cat ggc ctg gac atg<br>Gln Asp Glu Thr Cys Asp Thr Thr Thr Thr Asn His Gly Leu Asp Met<br>       135                  140                  145 | 607 |
| gag gag acg atg gtg gaa gct att tat aca ccg gaa cag agc gaa ggt<br>Glu Glu Thr Met Val Glu Ala Ile Tyr Thr Pro Glu Gln Ser Glu Gly<br>   150                    155                   160 | 655 |
| gcg ttt tat atg gat gag gag aca atg ttt ggg atg ccg act ttg ttg<br>Ala Phe Tyr Met Asp Glu Glu Thr Met Phe Gly Met Pro Thr Leu Leu<br>165                   170                  175                180 | 703 |
| gat aat atg gct gaa ggc atg ctt tta ccg ccg ccg tct gtt caa tgg<br>Asp Asn Met Ala Glu Gly Met Leu Leu Pro Pro Pro Ser Val Gln Trp<br>                 185                  190                195 | 751 |
| aat cat aat tat gac ggc gaa gga gat ggt gac gtg tcg ctt tgg agt<br>Asn His Asn Tyr Asp Gly Glu Gly Asp Gly Asp Val Ser Leu Trp Ser<br>            200                   205                 210 | 799 |
| tac taatattcga tagtcgtttc cattttgta ctatagtttg aaatattct<br>Tyr | 852 |
| agttcctttt tttagaatgg ttccttcatt ttatttatt ttattgttgt agaaacgagt | 912 |
| ggaaataat tcaatacaaa aaaaa | 937 |

<210> SEQ ID NO 6

```
<211> LENGTH: 213
<212> TYPE: PRT
<213> ORGANISM: Arabidopsis thaliana

<400> SEQUENCE: 6

Met Asn Ser Phe Ser Ala Phe Ser Glu Met Phe Gly Ser Asp Tyr Glu
  1               5                  10                  15

Pro Gln Gly Gly Asp Tyr Cys Pro Thr Leu Ala Thr Ser Cys Pro Lys
             20                  25                  30

Lys Pro Ala Gly Arg Lys Lys Phe Arg Glu Thr Arg His Pro Ile Tyr
         35                  40                  45

Arg Gly Val Arg Gln Arg Asn Ser Gly Lys Trp Val Ser Glu Val Arg
     50                  55                  60

Glu Pro Asn Lys Lys Thr Arg Ile Trp Leu Gly Thr Phe Gln Thr Ala
 65                  70                  75                  80

Glu Met Ala Ala Arg Ala His Asp Val Ala Ala Leu Ala Leu Arg Gly
                 85                  90                  95

Arg Ser Ala Cys Leu Asn Phe Ala Asp Ser Ala Trp Arg Leu Arg Ile
            100                 105                 110

Pro Glu Ser Thr Cys Ala Lys Asp Ile Gln Lys Ala Ala Ala Glu Ala
        115                 120                 125

Ala Leu Ala Phe Gln Asp Glu Thr Cys Asp Thr Thr Thr Asn His
    130                 135                 140

Gly Leu Asp Met Glu Glu Thr Met Val Glu Ala Ile Tyr Thr Pro Glu
145                 150                 155                 160

Gln Ser Glu Gly Ala Phe Tyr Met Asp Glu Thr Met Phe Gly Met
                165                 170                 175

Pro Thr Leu Leu Asp Asn Met Ala Glu Gly Met Leu Leu Pro Pro Pro
                180                 185                 190

Ser Val Gln Trp Asn His Asn Tyr Asp Gly Glu Gly Asp Gly Asp Val
            195                 200                 205

Ser Leu Trp Ser Tyr
    210

<210> SEQ ID NO 7
<211> LENGTH: 944
<212> TYPE: DNA
<213> ORGANISM: Arabidopsis thaliana
<220> FEATURE:
<221> NAME/KEY: CDS
<222> LOCATION: (135)..(782)

<400> SEQUENCE: 7
cctgaattag aaagaaaga tagatagaga aataaatatt ttatcatacc atacaaaaaa      60
agacagagat cttctactta ctctactctc ataaacctta tccagtttct tgaaacagag    120
tactcttctg atca atg aac tca ttt tct gcc ttt tct gaa atg ttt ggc     170
              Met Asn Ser Phe Ser Ala Phe Ser Glu Met Phe Gly
                1               5                  10 tcc gat tac gag tct ccg gtt tcc tca ggc ggt gat tac agt ccg aag     218
Ser Asp Tyr Glu Ser Pro Val Ser Ser Gly Gly Asp Tyr Ser Pro Lys
            15                  20                  25 ctt gcc acg agc tgc ccc aag aaa cca gcg gga agg aag aag ttt cgt     266
Leu Ala Thr Ser Cys Pro Lys Lys Pro Ala Gly Arg Lys Lys Phe Arg
 30                  35                  40 gag act cgt cac cca att tac aga gga gtt cgt caa aga aac tcc ggt     314
Glu Thr Arg His Pro Ile Tyr Arg Gly Val Arg Gln Arg Asn Ser Gly
 45                  50                  55                  60
```

-continued

```
aag tgg gtg tgt gag ttg aga gag cca aac aag aaa acg agg att tgg      362
Lys Trp Val Cys Glu Leu Arg Glu Pro Asn Lys Lys Thr Arg Ile Trp
             65                  70                  75 ctc ggg act ttc caa acc gct gag atg gca gct cgt gct cac gac gtc      410
Leu Gly Thr Phe Gln Thr Ala Glu Met Ala Ala Arg Ala His Asp Val
         80                  85                  90 gcc gcc ata gct ctc cgt ggc aga tct gcc tgt ctc aat ttc gct gac      458
Ala Ala Ile Ala Leu Arg Gly Arg Ser Ala Cys Leu Asn Phe Ala Asp
             95                 100                 105 tcg gct tgg cgg cta cga atc ccg gaa tca acc tgt gcc aag gaa atc      506
Ser Ala Trp Arg Leu Arg Ile Pro Glu Ser Thr Cys Ala Lys Glu Ile
    110                 115                 120 caa aag gcg gcg gct gaa gcc gcg ttg aat ttt caa gat gag atg tgt      554
Gln Lys Ala Ala Ala Glu Ala Ala Leu Asn Phe Gln Asp Glu Met Cys
125                 130                 135                 140 cat atg acg acg gat gct cat ggt ctt gac atg gag gag acc ttg gtg      602
His Met Thr Thr Asp Ala His Gly Leu Asp Met Glu Glu Thr Leu Val
                145                 150                 155 gag gct att tat acg ccg gaa cag agc caa gat gcg ttt tat atg gat      650
Glu Ala Ile Tyr Thr Pro Glu Gln Ser Gln Asp Ala Phe Tyr Met Asp
            160                 165                 170 gaa gag gcg atg ttg ggg atg tct agt ttg ttg gat aac atg gcc gaa      698
Glu Glu Ala Met Leu Gly Met Ser Ser Leu Leu Asp Asn Met Ala Glu
        175                 180                 185 ggg atg ctt tta ccg tcg ccg tcg gtt caa tgg aac tat aat ttt gat      746
Gly Met Leu Leu Pro Ser Pro Ser Val Gln Trp Asn Tyr Asn Phe Asp
    190                 195                 200 gtc gag gga gat gat gac gtg tcc tta tgg agc tat taaaattcga           792
Val Glu Gly Asp Asp Asp Val Ser Leu Trp Ser Tyr
205                 210                 215 tttttatttc cattttggt attatagctt tttatacatt tgatccttt ttagaatgga      852 tcttcttctt tttggttg tgagaaacga atgtaaatgg taaagttgt tgtcaaatgc       912 aaatgttttt gagtgcagaa tatataatct tt                                  944
```

<210> SEQ ID NO 8
<211> LENGTH: 216
<212> TYPE: PRT
<213> ORGANISM: Arabidopsis thaliana

<400> SEQUENCE: 8

```
Met Asn Ser Phe Ser Ala Phe Ser Glu Met Phe Gly Ser Asp Tyr Glu
1               5                   10                  15

Ser Pro Val Ser Ser Gly Gly Asp Tyr Ser Pro Lys Leu Ala Thr Ser
            20                  25                  30

Cys Pro Lys Lys Pro Ala Gly Arg Lys Lys Phe Arg Glu Thr Arg His
        35                  40                  45

Pro Ile Tyr Arg Gly Val Arg Gln Arg Asn Ser Gly Lys Trp Val Cys
    50                  55                  60

Glu Leu Arg Glu Pro Asn Lys Lys Thr Arg Ile Trp Leu Gly Thr Phe
65                  70                  75                  80

Gln Thr Ala Glu Met Ala Ala Arg Ala His Asp Val Ala Ala Ile Ala
                85                  90                  95

Leu Arg Gly Arg Ser Ala Cys Leu Asn Phe Ala Asp Ser Ala Trp Arg
            100                 105                 110

Leu Arg Ile Pro Glu Ser Thr Cys Ala Lys Glu Ile Gln Lys Ala Ala
        115                 120                 125

Ala Glu Ala Ala Leu Asn Phe Gln Asp Glu Met Cys His Met Thr Thr
```

```
                    130                 135                 140
Asp Ala His Gly Leu Asp Met Glu Glu Thr Leu Val Glu Ala Ile Tyr
145                 150                 155                 160

Thr Pro Glu Gln Ser Gln Asp Ala Phe Tyr Met Asp Glu Glu Ala Met
                165                 170                 175

Leu Gly Met Ser Ser Leu Leu Asp Asn Met Ala Glu Gly Met Leu Leu
            180                 185                 190

Pro Ser Pro Ser Val Gln Trp Asn Tyr Asn Phe Asp Val Glu Gly Asp
        195                 200                 205

Asp Asp Val Ser Leu Trp Ser Tyr
    210                 215

<210> SEQ ID NO 9
<211> LENGTH: 1513
<212> TYPE: DNA
<213> ORGANISM: Arabidopsis thaliana
<220> FEATURE:
<221> NAME/KEY: CDS
<222> LOCATION: (183)..(1172)
<221> NAME/KEY: modified_base
<222> LOCATION: 1440
<223> OTHER INFORMATION: n represents a, g, c or t
<221> NAME/KEY: modified_base
<222> LOCATION: 1443
<223> OTHER INFORMATION: n represents a, g, c or t
<221> NAME/KEY: modified_base
<222> LOCATION: 1444
<223> OTHER INFORMATION: n represents a, g, c or t
<221> NAME/KEY: modified_base
<222> LOCATION: 1447
<223> OTHER INFORMATION: n represents a, g, c or t
<221> NAME/KEY: modified_base
<222> LOCATION: 1450
<223> OTHER INFORMATION: n represents a, g, c or t
<221> NAME/KEY: modified_base
<222> LOCATION: 1459
<223> OTHER INFORMATION: n represents a, g, c or t
<221> NAME/KEY: modified_base
<222> LOCATION: 1472
<223> OTHER INFORMATION: n represents a, g, c or t
<221> NAME/KEY: modified_base
<222> LOCATION: 1495
<223> OTHER INFORMATION: n represents a, g, c or t
<221> NAME/KEY: modified_base
<222> LOCATION: 1508
<223> OTHER INFORMATION: n represents a, g, c or t
<221> NAME/KEY: modified_base
<222> LOCATION: 1510
<223> OTHER INFORMATION: n represents a, g, c or t

<400> SEQUENCE: 9
gagacgctag aaagaacgcg aaagcttgcg aagaagattt gcttttgatc gacttaacac      60
gaacaacaaa caacatctgc gtgataaaga agagatttt gcctaaataa agaagagatt     120
cgactctaat cctggagtta tcattcacga tagattctta gattgcgact ataaagaaga    180 ag atg gct gta tat gaa caa acc gga acc gag cag ccg aag aaa agg      227
   Met Ala Val Tyr Glu Gln Thr Gly Thr Glu Gln Pro Lys Lys Arg
   1               5                  10                  15 aaa tct agg gct cga gca ggt ggt tta acg gtg gct gat agg cta aag    275
Lys Ser Arg Ala Arg Ala Gly Gly Leu Thr Val Ala Asp Arg Leu Lys
                20                  25                  30 aag tgg aaa gag tac aac gag att gtt gaa gct tcg gct gtt aaa gaa    323
Lys Trp Lys Glu Tyr Asn Glu Ile Val Glu Ala Ser Ala Val Lys Glu
            35                  40                  45 gga gag aaa ccg aaa cgc aaa gtt cct gcg aaa ggg tcg aag aaa ggt    371
Gly Glu Lys Pro Lys Arg Lys Val Pro Ala Lys Gly Ser Lys Lys Gly
        50                  55                  60
```

```
tgt atg aag ggt aaa gga gga cca gat aat tct cac tgt agt ttt aga       419
Cys Met Lys Gly Lys Gly Gly Pro Asp Asn Ser His Cys Ser Phe Arg
     65                  70                  75 gga gtt aga caa agg att tgg ggt aaa tgg gtt gca gag att cga gaa       467
Gly Val Arg Gln Arg Ile Trp Gly Lys Trp Val Ala Glu Ile Arg Glu
 80                  85                  90                  95 ccg aaa ata gga act aga ctt tgg ctt ggt act ttt cct acc gcg gaa       515
Pro Lys Ile Gly Thr Arg Leu Trp Leu Gly Thr Phe Pro Thr Ala Glu
                100                 105                 110 aaa gct gct tcc gct tat gat gaa gcg gct acc gct atg tac ggt tca       563
Lys Ala Ala Ser Ala Tyr Asp Glu Ala Ala Thr Ala Met Tyr Gly Ser
            115                 120                 125 ttg gct cgt ctt aac ttc cct cag tct gtt ggg tct gag ttt act agt       611
Leu Ala Arg Leu Asn Phe Pro Gln Ser Val Gly Ser Glu Phe Thr Ser
        130                 135                 140 acg tct agt caa tct gag gtg tgt acg gtt gaa aat aag gcg gtt gtt       659
Thr Ser Ser Gln Ser Glu Val Cys Thr Val Glu Asn Lys Ala Val Val
    145                 150                 155 tgt ggt gat gtt tgt gtg aag cat gaa gat act gat tgt gaa tct aat       707
Cys Gly Asp Val Cys Val Lys His Glu Asp Thr Asp Cys Glu Ser Asn
160                 165                 170                 175 cca ttt agt cag att tta gat gtt aga gaa gag tct tgt gga acc agg       755
Pro Phe Ser Gln Ile Leu Asp Val Arg Glu Glu Ser Cys Gly Thr Arg
                180                 185                 190 ccg gac agt tgc acg gtt gga cat caa gat atg aat tct tcg ctg aat       803
Pro Asp Ser Cys Thr Val Gly His Gln Asp Met Asn Ser Ser Leu Asn
            195                 200                 205 tac gat ttg ctg tta gag ttt gag cag cag tat tgg ggc caa gtt ttg       851
Tyr Asp Leu Leu Leu Glu Phe Glu Gln Gln Tyr Trp Gly Gln Val Leu
        210                 215                 220 cag gag aaa gag aaa ccg aag cag gaa gaa gag gag ata cag caa cag       899
Gln Glu Lys Glu Lys Pro Lys Gln Glu Glu Glu Glu Ile Gln Gln Gln
    225                 230                 235 caa cag gaa cag caa cag caa cag ctg caa ccg gat ttg ctt act gtt       947
Gln Gln Glu Gln Gln Gln Gln Gln Leu Gln Pro Asp Leu Leu Thr Val
240                 245                 250                 255 gca gat tac ggt tgg cct tgg tct aat gat att gta aat gat cag act       995
Ala Asp Tyr Gly Trp Pro Trp Ser Asn Asp Ile Val Asn Asp Gln Thr
                260                 265                 270 tct tgg gat cct aat gag tgc ttt gat att aat gaa ctc ctt gga gat      1043
Ser Trp Asp Pro Asn Glu Cys Phe Asp Ile Asn Glu Leu Leu Gly Asp
            275                 280                 285 ttg aat gaa cct ggt ccc cat cag agc caa gac caa aac cac gta aat      1091
Leu Asn Glu Pro Gly Pro His Gln Ser Gln Asp Gln Asn His Val Asn
        290                 295                 300 tct ggt agt tat gat ttg cat ccg ctt cat ctc gag cca cac gat ggt      1139
Ser Gly Ser Tyr Asp Leu His Pro Leu His Leu Glu Pro His Asp Gly
    305                 310                 315 cac gag ttc aat ggt ttg agt tct ctg gat att tgagagttct gaggcaatgg    1192
His Glu Phe Asn Gly Leu Ser Ser Leu Asp Ile
320                 325                 330 tcctacaaga ctacaacata atctttggat tgatcatagg agaaacaaga aataggtgtt    1252
aatgatctga ttcacaatga aaaatatttt aataactcta tagttttttgt tctttccttg   1312 gatcatgaac tgttgcttct catctattga gttaatatag cgaatagcag agtttctctc    1372
tttcttctct ttgtagaaaa aaaaaaaaaa aaaaaaaaaa aaaaaaaayh sakmabgcar    1432
srcsdvsnaa nntrnatnar sarchcntrr agrctrascn csrcaswash tskbabarak   1492
```
aantamaysa kmasrngnga c                                                      1513

<210> SEQ ID NO 10
<211> LENGTH: 330
<212> TYPE: PRT
<213> ORGANISM: Arabidopsis thaliana

<400> SEQUENCE: 10

Met Ala Val Tyr Glu Gln Thr Gly Thr Glu Gln Pro Lys Lys Arg Lys
1               5                   10                  15

Ser Arg Ala Arg Ala Gly Gly Leu Thr Val Ala Asp Arg Leu Lys Lys
            20                  25                  30

Trp Lys Glu Tyr Asn Glu Ile Val Glu Ala Ser Ala Val Lys Glu Gly
        35                  40                  45

Glu Lys Pro Lys Arg Lys Val Pro Ala Lys Gly Ser Lys Lys Gly Cys
    50                  55                  60

Met Lys Gly Lys Gly Gly Pro Asp Asn Ser His Cys Ser Phe Arg Gly
65                  70                  75                  80

Val Arg Gln Arg Ile Trp Gly Lys Trp Val Ala Glu Ile Arg Glu Pro
                85                  90                  95

Lys Ile Gly Thr Arg Leu Trp Leu Gly Thr Phe Pro Thr Ala Glu Lys
            100                 105                 110

Ala Ala Ser Ala Tyr Asp Glu Ala Ala Thr Ala Met Tyr Gly Ser Leu
        115                 120                 125

Ala Arg Leu Asn Phe Pro Gln Ser Val Gly Ser Glu Phe Thr Ser Thr
    130                 135                 140

Ser Ser Gln Ser Glu Val Cys Thr Val Glu Asn Lys Ala Val Val Cys
145                 150                 155                 160

Gly Asp Val Cys Val Lys His Glu Asp Thr Asp Cys Glu Ser Asn Pro
                165                 170                 175

Phe Ser Gln Ile Leu Asp Val Arg Glu Glu Ser Cys Gly Thr Arg Pro
            180                 185                 190

Asp Ser Cys Thr Val Gly His Gln Asp Met Asn Ser Ser Leu Asn Tyr
        195                 200                 205

Asp Leu Leu Leu Glu Phe Glu Gln Gln Tyr Trp Gly Gln Val Leu Gln
    210                 215                 220

Glu Lys Glu Lys Pro Lys Gln Glu Glu Glu Ile Gln Gln Gln Gln
225                 230                 235                 240

Gln Glu Gln Gln Gln Gln Leu Gln Pro Asp Leu Leu Thr Val Ala
                245                 250                 255

Asp Tyr Gly Trp Pro Trp Ser Asn Asp Ile Val Asn Asp Gln Thr Ser
            260                 265                 270

Trp Asp Pro Asn Glu Cys Phe Asp Ile Asn Glu Leu Leu Gly Asp Leu
        275                 280                 285

Asn Glu Pro Gly Pro His Gln Ser Gln Asp Gln Asn His Val Asn Ser
    290                 295                 300

Gly Ser Tyr Asp Leu His Pro Leu His Leu Glu Pro His Asp Gly His
305                 310                 315                 320

Glu Phe Asn Gly Leu Ser Ser Leu Asp Ile
                325                 330

<210> SEQ ID NO 11
<211> LENGTH: 30
<212> TYPE: DNA
<213> ORGANISM: Artificial Sequence
<220> FEATURE:

-continued

```
<223> OTHER INFORMATION: Designed oligonucleotide based on the promoter
      region of rd29A gene and having a HindIII site.

<400> SEQUENCE: 11
aagcttaagc ttacatcagt ttgaaagaaa                                    30

<210> SEQ ID NO 12
<211> LENGTH: 31
<212> TYPE: DNA
<213> ORGANISM: Artificial Sequence
<220> FEATURE:
<223> OTHER INFORMATION: Designed oligonucleotide based on the promoter
      region of rd29A gene and having a HindIII site.

<400> SEQUENCE: 12
aagcttaagc ttgctttttg gaactcatgt c                                  31
```